(12) United States Patent
Hall et al.

(10) Patent No.: US 11,166,653 B2
(45) Date of Patent: Nov. 9, 2021

(54) RECONFIGURABLE, MULTI-TECHNIQUE ELECTROCHEMICAL PORTABLE BIOSENSOR

(71) Applicant: The Regents of the University of California, Oakland, CA (US)

(72) Inventors: Drew Hall, Oakland, CA (US); Alexander Chuan Sun, Oakland, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 531 days.

(21) Appl. No.: 15/768,507

(22) PCT Filed: Oct. 12, 2016

(86) PCT No.: PCT/US2016/056678
§ 371 (c)(1),
(2) Date: Apr. 13, 2018

(87) PCT Pub. No.: WO2017/066347
PCT Pub. Date: Apr. 20, 2017

(65) Prior Publication Data
US 2018/0303386 A1   Oct. 25, 2018

Related U.S. Application Data

(60) Provisional application No. 62/241,609, filed on Oct. 14, 2015.

(51) Int. Cl.
*A61B 5/1477* (2006.01)
*A61B 5/145* (2006.01)
*A61B 5/00* (2006.01)

(52) U.S. Cl.
CPC ........ *A61B 5/1477* (2013.01); *A61B 5/14517* (2013.01); *A61B 5/14532* (2013.01);
(Continued)

(58) Field of Classification Search
CPC . A61B 5/1477; A61B 5/6898; A61B 5/14517; A61B 5/14532; A61B 5/14539;
(Continued)

(56) References Cited

U.S. PATENT DOCUMENTS 8,923,918 B2   12/2014   Kreger et al.
8,947,656 B2   2/2015    Cunningham
(Continued)

FOREIGN PATENT DOCUMENTS

WO   2015086269 A1   6/2015
WO   2015112368 A1   6/2015

OTHER PUBLICATIONS

Written Opinion for PCT Application No. PCT/US2016/056678, dated Dec. 23, 2016, 5 pages.
(Continued)

*Primary Examiner* — Navin Natnithithadha
(74) *Attorney, Agent, or Firm* — Perkins Coie LLP

(57) ABSTRACT

Some embodiments relate to a reconfigurable biosensor adapted for performing tests in a plurality of modes or a smartphone or wearable device comprising the reconfigurable biosensor.

17 Claims, 18 Drawing Sheets

Block diagram of the biosensing module

(52) U.S. Cl.
CPC ........ *A61B 5/14539* (2013.01); *A61B 5/6898* (2013.01); *A61B 5/681* (2013.01); *A61B 5/6893* (2013.01); *A61B 2562/0295* (2013.01)

(58) Field of Classification Search
CPC .................. A61B 5/681; A61B 5/6893; A61B 2562/0295
USPC .......................................... 600/309, 345–366
See application file for complete search history.

(56) References Cited

U.S. PATENT DOCUMENTS

| | | | | |
|---|---|---|---|---|
| 9,810,656 | B2* | 11/2017 | Davis ................ | G01N 27/3276 |
| 10,364,452 | B2* | 7/2019 | Wang ..................... | C12Q 1/005 |
| 10,973,448 | B2* | 4/2021 | Soltani .................. | A61B 5/002 |
| 2013/0012796 | A1 | 1/2013 | Kak et al. | |
| 2014/0012511 | A1 | 1/2014 | Mensinger et al. | |
| 2014/0072308 | A1 | 3/2014 | Jain et al. | |
| 2014/0099237 | A1 | 4/2014 | Chang et al. | |
| 2014/0170761 | A1 | 6/2014 | Crawford et al. | |
| 2015/0001071 | A1 | 1/2015 | Le Neel et al. | |
| 2015/0122669 | A1* | 5/2015 | Davis ................ | G01N 27/3276 205/780.5 |
| 2015/0257687 | A1 | 9/2015 | Pushpala et al. | |
| 2016/0310048 | A1* | 10/2016 | Pang ........................ | A61B 5/07 |
| 2017/0226557 | A1* | 8/2017 | Wang ..................... | C12Q 1/005 |
| 2018/0214054 | A1* | 8/2018 | Soltani ................ | A61B 5/0536 |
| 2018/0263539 | A1* | 9/2018 | Javey ................. | A61B 5/14539 |

OTHER PUBLICATIONS

International Search Report for PCT Application No. PCT/US2016/056678, dated Dec. 23, 2016, 3 pages.
Ahmadi, et al., "Current-Mirror-Based Potentiostats for Three-Electrode Amperometric Electrochemical Sensors," IEEE Trans. Circuits Syst. Regul. Pap., vol. 56, No. 7, pp. 1339-1348, Jul. 2009.
Angelini, et al., "An Arduino-based EIS with a logarithmic amplifier for corrosion monitoring," in Instrumentation and Measurement Technology Conference (I2MTC) Proceedings, 2014 IEEE International, 2014, pp. 905-910.
Arao, et al., "Measurement of Urinary Lactoferrin as a Marker of Urinary Tract Infection," J. Clin. Microbiol., vol. 37, No. 3, pp. 553-557, Mar. 1999.
Berg, et al., "Cellphone-Based Hand-Held Microplate Reader for Point-of-Care Testing of Enzyme-Linked Immunosorbent Assays," ACS Nano, vol. 9, No. 8, pp. 7857-7866, Aug. 2015.
Blanco, et al., "Design of a Low-Cost Portable Potentiostat for Amperometric Biosensors," in Proceedings of the IEEE Instrumentation and Measurement Technology Conference, 2006. IMTC 2006, 2006, pp. 690-694.
Bryan, et al., "An optimised electrochemical biosensor for the label-free detection of C-reactive protein in blood," Biosens. Bioelectron., vol. 39, No. 1, pp. 94-98, Jan. 2013.
Carullo, et al., "Low-cost electrochemical impedance spectroscopy system for corrosion monitoring of metallic antiquities and works of art," IEEE Trans. Instrum. Meas., vol. 49, No. 2, pp. 371-375, Apr. 2000.
Cevenini, et al., "Smartphone-interfaced 3D printed toxicity biosensor integrating bioluminescent 'sentinel cells,'" Sens. Actuators B Chem., 2016, pp. 249-257.
Cruz, et al., "A low-cost miniaturized potentiostat for point-of-care diagnosis," Biosensors and Bioelectronics, vol. 62, pp. 249-254, Dec. 2014.
Daniels, et al., "Simultaneous measurement of nonlinearity and electrochemical impedance for protein sensing using two-tone excitation," in 30th Annual International Conference of the IEEE Engineering in Medicine and Biology Society, 2008. EMBS 2008, 2008, pp. 5753-5756.
Daniels, et al., "Label-Free Impedance Biosensors: Opportunities and Challenges," Electroanalysis, vol. 19, No. 12, pp. 1239-1257, 2007.
Das, et al., "Electrochemical Immunosensor Using p Aminophenol Redox Cycling by Hydrazine Combined with a Low Background Current," Anal. Chem., vol. 79, No. 7, pp. 2790-2796, Apr. 2007.
Doeven, et al., "Mobile phone-based electrochemiluminescence sensing exploiting the 'USB On-The-Go' protocol," Sens. Actuators B Chem., vol. 216, pp. 608-613, Sep. 2015.
Huang, et al., "A Portable Potentiostat with Molecularly Imprinted Polymeric Electrode for Dopamine Sensing," in IEEE Circuits and Systems International Conference on Testing and Diagnosis, 2009. ICTD 2009, 2009, pp. 1-4.
Hwang, et al., "CMOS VLSI Potentiostat for Portable Environmental Sensing Applications," IEEE Sens. J., vol. 10, No. 4, pp. 820-821,2010.
Ionescu, et al., "Portable measuring and display unit for electrochemical sensors," in Design and Technology in Electronic Packaging (SIITME), 2010 IEEE 16th International Symposium for, 2010, pp. 215-218.
Jafari, et al., "16-Channel CMOS Impedance Spectroscopy DNA Analyzer With Dual-Slope Multiplying ADCs," IEEE Trans. Biomed. Circuits Syst., vol. 6, No. 5, pp. 468-478, Oct. 2012.
Joishy, et al., "Fecal Calprotectin and Lactoferrin as Noninvasive Markers of Pediatric Inflammatory Bowel Disease:," J. Pediatr. Gastroenterol. Nutr., vol. 48, No. 1, pp. 48-54, Jan. 2009.
Katz, et al., "Probing Biomolecular Interactions at Conductive and Semiconductive Surfaces by Impedance Spectroscopy: Routes to Impedimetric Immunosensors, DNA-Sensors, and Enzyme Biosensors," Electroanalysis, vol. 15, No. 11, pp. 913-947, 2003.
Kijlstra, et al., "Lactoferrin levels in normal human tears.," Br. J. Ophthalmol., vol. 67, No. 3, pp. 199-202, Mar. 1983.
Li, et al., "CMOS Amperometric Instrumentation and Packaging for Biosensor Array Applications," IEEE Trans. Biomed. Circuits Syst., vol. 5, No. 5, pp. 439-448, Oct. 2011.
Lillehoj, et al., "Rapid electrochemical detection on a mobile phone," Lab. Chip, vol. 13, No. 15, pp. 2950-2955, Jul. 2013.
Ludwig, et al., "Cellphone-based detection platform for rbST biomarker analysis in milk extracts using a microsphere fluorescence immunoassay," Anal. Bioanal. Chem., vol. 406, No. 27, pp. 6857-6866, Jun. 2014.
Ludwig, et al., "Calling Biomarkers in Milk Using a Protein Microarray on Your Smartphone," PLoS ONE, vol. 10, No. 8, p. e0134360, Aug. 2015.
Manickam, et al., "A CMOS Electrochemical Impedance Spectroscopy (EIS) Biosensor Array," IEEE Trans. Biomed. Circuits Syst., vol. 4, No. 6, pp. 379-390, Dec. 2010.
McGeough, et al., "Camera Phone-Based Quantitative Analysis of C Reactive Protein ELISA," IEEE Trans. Biomed. Circuits Syst., vol. 7, No. 5, pp. 655-659, Oct. 2013.
Mizuhashi, et al., "Levels of the antimicrobial proteins lactoferrin and chromogranin in the saliva of individuals with oral dryness," J. Prosthet. Dent. 2015, pp. 35-38.
Nazari, et al., "CMOS Neurotransmitter Microarray: 96-Channel Integrated Potentiostat With On-Die Microsensors," IEEE Trans. Biomed. Circuits Syst., vol. 7, No. 3, pp. 338-348, Jun. 2013.
Nemiroski, et al., "Universal mobile electrochemical detector designed for use in resource-limited applications," Proc. Natl. Acad. Sci., vol. 111, No. 33, p. 11984-11989, Aug. 2014.
Ohno, et al., "Electrochemical impedance spectroscopy biosensor with interdigitated electrode for detection of human immunoglobulin A," Biosens. Bioelectron., vol. 40, No. 1, pp. 422-426, Feb. 2013.
Oncescu, et al., "Smartphone based health accessory for colorimetric detection of biomarkers in sweat and saliva," Lab. Chip, vol. 13, No. 16, pp. 3232-3238, Jul. 2013.
Oncescu, et al., "Cholesterol testing on a smartphone," Lab. Chip, vol. 14, No. 4, pp. 759-763, Jan. 2014.
Park, et al., "An antimicrobial protein, lactoferrin exists in the sweat: proteomic analysis of sweat," Exp. Dermatol., vol. 20, No. 4, pp. 369-371,2011.

(56) References Cited

OTHER PUBLICATIONS

Punter-Villagrasa, et al., "A portable point-of-use EIS device for in-vivo biom #x00E9;dical applications," in 2014 Conference on Design of Circuits and Integrated Circuits (DCIS), 2014, pp. 1-6.
Ramfos, et al., "A compact hybrid-multiplexed potentiostat for real-time electrochemical biosensing applications," Biosens. Bioelectron., vol. 47, pp. 482-489, Sep. 2013.
Rowe, et al., "CheapStat: An Open-Source, 'Do-It-Yourself' Potentiostat for Analytical and Educational Applications," PLoS ONE, vol. 6, No. 9, p. e23783, Sep. 2011.
Stanacevic, et al., "VLSI Potentiostat Array With Oversampling Gain Modulation for Wide-Range Neurotransmitter Sensing," IEEE Trans. Biomed. Circuits Syst., vol. 1, No. 1, pp. 63-72, Mar. 2007.
Steinberg, et al., "A wireless potentiostat for mobile chemical sensing and biosensing," Talanta, vol. 143, pp. 178-183, Oct. 2015.
Su, et al., "High-sensitive and high-efficient biochemical analysis method using a bionic electronic eye in combination with a smartphone-based colorimetric reader system," Sens. Actuators B Chem., vol. 216, pp. 134-140, Sep. 2015.
Sun, et al., "A low-cost smartphone-based electrochemical biosensor for point-of-care diagnostics," in 2014 IEEE Biomedical Circuits and Systems Conference (BioCAS), 2014, pp. 312-315.
Sun, et al., "A multitechnique reconfigurable electrochemical biosensor for integration into mobile technologies," in 2015 IEEE Biomedical Circuits and Systems Conference (BioCAS), 2015, pp. 1-4.
Vergani, et al., "Multichannel Bipotentiostat Integrated With a Microfluidic Platform for Electrochemical Real-Time Monitoring of Cell Cultures," IEEE Trans. Biomed. Circuits Syst., vol. 6, No. 5, pp. 498-507, Oct. 2012.
Wang, et al., "Audio jack based miniaturized mobile phone electrochemical sensing platform," Sens. Actuators B Chem., vol. 209, pp. 677-685, Mar. 2015.
Ward, et al., "Multiple Chronic Conditions Among US Adults: A 2012 Update," Prev. Chronic. Dis., vol. 11, Apr. 2014.
Xu, et al., "Simultaneous color sensing of O2 and pH using a smartphone," Sens. Actuators B Chem., vol. 220, pp. 326-330, Dec. 2015.
Xu, et al., "The label free picomolar detection of insulin in blood serum," Biosens. Bioelectron., vol. 39, No. 1, pp. 21-25, Jan. 2013.
Zangheri, et al., "A simple and compact smartphone accessory for quantitative chemiluminescence-based lateral flow immunoassay for salivary cortisol detection," Biosens. Bioelectron., vol. 64, pp. 63-68, Feb. 2015.
Zhang, et al., "Protein detecting with smartphone-controlled electrochemical impedance spectroscopy for point-of-care applications," Sens. Actuators B Chem., vol. 222, pp. 994-1002, Jan. 2016.

\* cited by examiner

Complete electrochemical biosensor platform with disposable electrodes, bisensor module, and modular mobile device such as Google ATAP's Project Ara Block diagram of the biosensing module Schematic of a) Amperometric, b) potentiometric, and c) impedance spectroscopy modes Photograph of the PCB prototype biosensor module a) Voltammograms at different scan rates; b) the anodic current peak plotted against scan rate measured by both the module and CHI pH calibration curve with fitted line a) Chronoamperometry curves for glucose measured by the sensing module and b) calibration curves for both the biosensor and CHI with the positive and negative diagnosis ranges annotated

RECONFIGURABLE, MULTI-TECHNIQUE ELECTROCHEMICAL PORTABLE BIOSENSOR

INCORPORATION BY REFERENCE TO ANY PRIORITY APPLICATIONS

This application is a 371 National Phase Application of PCT Application No. PCT/US2016/056678, entitled "RECONFIGURABLE, MULTI-TECHNIQUE ELECTROCHEMICAL PORTABLE BIOSENSOR", filed Oct. 12, 2016, which claims the benefit of priority to U.S. Provisional Application Ser. No. 62/241,609, entitled "RECONFIGURABLE, MULTITECHNIQUE ELECTROCHEMICAL PORTABLE BIOSENSOR," filed Oct. 14, 2015. The entire content of the aforementioned patent applications is incorporated by reference herein in their entirety.

BACKGROUND

Field

Some embodiments described herein relate to a reconfigurable multitechnique electrochemical biosensor integrated into a smartphone, wearable device, textile, home appliance, vehicle, autonomous vehicle, or any other system comprising the reconfigurable bionsensor.

Description of the Related Art

While current mobile devices include certain sensors therein, there remains a need for smartphones, wearable devices, and other platforms that include biosensors for a plurality of functions, such as point-of-care testing.

SUMMARY

Some embodiments are described in the following numbered Paragraphs:

1. A smartphone or wearable device comprising an integrated reconfigurable biosensor adapted for performing tests in a plurality of modes.
2. The smartphone or wearable device of Paragraph 1, wherein said plurality of modes can be implemented without the addition of further high power components into a circuit comprising said integrated reconfigurable biosensor.
3. The smartphone or wearable device of any one of Paragraphs 1 and 2, wherein said plurality of modes comprise amperometric measurements, potentiometric measurements, and impedance spectroscopy.
4. The smartphone or wearable device of any one of Paragraphs 1-3 wherein each of the modes can be implemented without the addition of any further components into a circuit comprising said integrated reconfigurable biosensor.
5. The smartphone or wearable device of any one of Paragraphs 1-4, wherein said smartphone comprises a Google Project Ara™ smartphone.
6. The smartphone or wearable device of any one of Paragraphs 1-5, wherein said reconfigurable biosensor comprises a potentiostat adapted to perform a plurality of electrochemical detection techniques.
7. The smartphone or wearable device of any one of Paragraphs 1-6, wherein said reconfigurable biosensor is adapted for high-speed communication with said smartphone or wearable device.
8. The smartphone or wearable device of any one of Paragraphs 1-7, wherein said reconfigurable biosensor is adapted to interface with a plurality of external test chips or electrodes.
9. The smartphone or wearable device of any one of Paragraphs 1-8, wherein said reconfigurable biosensor is adapted for performing a test selected from the group consisting of measuring glucose levels, cyclic voltammetry, chronoampermetry, square wave voltammetry, differential pulse voltammetry and measuring pH.
10. The smartphone or wearable device of any one of Paragraphs 1-9, wherein said reconfigurable biosensor is adapted to perform an analysis such as glucose testing, health and wellness monitoring, monitoring the chronic diseases such as Cystic Fibrosis, monitoring inflammation, assessing food or water safety, detection of heavy metal or *salmonella* in the environment or produce, daily health tracking, measuring cholesterol or hydration levels, detecting an infectious or pathogenic agent, detecting malaria, detecting HIV, detecting HCV, and detecting TB.
11. The smartphone or wearable device of any one of Paragraphs 1-10, wherein said reconfigurable biosensor comprises two working electrodes (WE) with each channel having independently configurable gain.
12. The smartphone or wearable device of any one of Paragraphs 1-11, wherein said biosensor comprises a digital to analog converter and an analog to digital converter.
13. The smartphone or wearable device of any one of Paragraphs 1-12, wherein said biosensor comprises a microcontroller.
14. A reconfigurable biosensor adapted for performing tests in a plurality of modes.
15. The reconfigurable biosensor of Paragraph 14, wherein said plurality of modes can be implemented without the addition of further high power components into a circuit comprising said integrated reconfigurable biosensor.
16. The reconfigurable biosensor of any one of Paragraphs 14 and 15, wherein said plurality of modes comprise amperometric measurements, potentiometric measurements, and impedance spectroscopy.
17. The reconfigurable biosensor of any one of Paragraphs 14-16 wherein each of the modes can be implemented without the addition of any further components into a circuit comprising said integrated reconfigurable biosensor.
18. The reconfigurable biosensor of any one of Paragraphs 14-17, wherein said smartphone comprises a Project Ara smartphone.
19. The reconfigurable biosensor of any one of Paragraphs 14-18, wherein said reconfigurable biosensor comprises a potentiostat adapted to perform a plurality of electrochemical detection techniques.
20. The reconfigurable biosensor of any one of Paragraphs 14-19, wherein said reconfigurable biosensor is adapted for high-speed communication with said smartphone or wearable device.
21. The reconfigurable biosensor of any one of Paragraphs 14-20, wherein said reconfigurable biosensor is adapted to interface with a plurality of external test chips or electrodes.
22. The reconfigurable biosensor of any one of Paragraphs 14-21, wherein said reconfigurable biosensor is adapted for performing a test selected from the group consisting of measuring glucose levels, cyclic voltammetry and measuring pH.
23. The reconfigurable biosensor of any one of Paragraphs 14-22, wherein said reconfigurable biosensor is adapted to perform an analysis selected from the group consisting of glucose testing, health and wellness monitoring, monitoring the status of Cystic Fibrosis, monitoring inflammation, assessing food or water safety, detection of heavy metal or *salmonella* in the environment or produce, daily health tracking, measuring cholesterol or hydration levels, detecting an infectious or pathogenic agent, detecting malaria, detecting HIV, detecting HCV, and detecting TB.

24. The reconfigurable biosensor of any one of Paragraphs 14-23, wherein said reconfigurable biosensor comprises two working electrodes (WE) with each channel having independently configurable gain.

25. The reconfigurable biosensor of any one of Paragraphs 14-24, wherein said biosensor comprises a digital to analog converter and an analog to digital converter.

26. The reconfigurable biosensor of any one of Paragraphs 14-25, wherein said biosensor comprises a microcontroller.

27. A method of performing a biological analysis comprising performing said biological analysis on a subject or a biological sample obtained from a subject using a smartphone or wearable device of any one of Paragraphs 1-13 or a reconfigurable biosensor of any one of Paragraphs 14-25.

28. The method of Paragraph 27, wherein said biological analysis is performed by placing said smartphone or wearable device of any one of Paragraphs 1-13 or a reconfigurable biosensor of any one of Paragraphs 14-25 in contact with a portion of said subject's body.

29. A system for performing electrochemical sensing tests on a subject's body, comprising: a portable electronic platform; and a reconfigurable biosensing circuit configured to have an amperometric mode to perform a amperometric measurement, a potentiometric mode to perform a potentiometric measurement, and electrochemical impedance spectroscopy (EIS) mode to perform EIS on the body.

30. The system of Paragraph 29, further comprising a disposable test chip configured to connect to the biosensing circuit.

31. The system of any one of Paragraphs 29-30, wherein the reconfigurable biosensing circuit comprises a potentiostat.

32. The system of any one of Paragraphs 29-31, wherein the reconfigurable biosensing circuit comprises two working electrodes and two resistive feedback transimpedance amplifiers (TIAs) connected to a respective working electrode, and wherein each TIA has an independently adjustable gain and bandwidth.

33. The system of any one of Paragraphs 29-32, wherein the two working electrodes are configured to be run simultaneously.

34. The system of any one of Paragraphs 29-33, wherein the reconfigurable biosensing circuit further comprises a reference electrode and a counter electrode to set a potential for the reconfigurable biosensing circuit.

35. The system of any one of Paragraphs 29-34, wherein the reconfigurable biosensing circuit further comprises an input buffer connected to the reference electrode in the amperometric mode, and wherein the input buffer is configured as a high impedance input for an op-amp in the potentiometric mode.

36. The system of any one of Paragraphs 29-35, wherein the reference electrode is configured to be floating in the EIS mode.

37. The system of any one of Paragraphs 29-36, wherein a first two-electrode sensor is attached between the counter electrode and a first one of the working electrodes.

38. The system of any one of Paragraphs 29-37, wherein a second two-electrode sensor is attached between the counter electrode and a second one of the working electrodes.

39. The system of any one of Paragraphs 29-38, wherein the portable electronic platform comprises smartphone, smartwatch, personal digital assistant (PDA), tablet computer, textile including electronic components or any wearable technology.

40. A smartphone or wearable device comprising an integrated reconfigurable electrochemical biosensor adapted for performing a plurality of measurement techniques.

41. The smartphone or wearable device of Paragraph 40, further comprising a circuit comprising said integrated reconfigurable electrochemical biosensor, wherein said plurality of measurement techniques is implemented without redundancy for the plurality of measurement techniques in the circuit.

42. The smartphone or wearable device of any one of Paragraphs 40 and 41, wherein said plurality of measurement techniques comprise amperometric measurements, potentiometric measurements, and impedance spectroscopy.

43. The smartphone or wearable device of any one of Paragraphs 40-42, wherein said smartphone comprises a Google's Project Ara™ smartphone.

44. The smartphone or wearable device of any one of Paragraphs 40-43, wherein said reconfigurable electrochemical biosensor comprises a potentiostat adapted to perform a plurality of electrochemical detection techniques.

45. The smartphone or wearable device of any one of Paragraphs 40-44, wherein said reconfigurable electrochemical biosensor is adapted for high-speed communication with said smartphone or wearable device.

46. The smartphone or wearable device of any one of Paragraphs 40-45, wherein said reconfigurable electrochemical biosensor is adapted to interface with a plurality of external test strips or electrodes.

47. The smartphone or wearable device of any one of Paragraphs 40-46, wherein said reconfigurable electrochemical biosensor is adapted for performing a test selected from the group consisting of cyclic voltammetry, chronoamperometry, square wave voltammetry and differential pulse voltammetry.

48. The smartphone or wearable device of any one of Paragraphs 40-47, wherein said reconfigurable electrochemical biosensor is adapted to perform an analysis selected from the group consisting of glucose testing, pH testing, health and wellness monitoring, monitoring chronic diseases, monitoring Cystic Fibrosis, monitoring inflammation, assessing food or water safety, detection of heavy metal or *salmonella* in the environment or produce, daily health tracking, measuring cholesterol or hydration levels, detecting an infectious or pathogenic agent, detecting malaria, detecting HIV, detecting HCV, and detecting TB.

49. The smartphone or wearable device of any one of Paragraphs 40-48, wherein said reconfigurable electrochemical biosensor comprises two working electrodes (WE) with each channel having independently configurable gain.

50. The smartphone or wearable device of any one of Paragraphs 40-49, wherein said reconfigurable electrochemical biosensor comprises a digital to analog converter and an analog to digital converter.

51. The smartphone or wearable device of any one of Paragraphs 40-50, wherein said reconfigurable electrochemical biosensor comprises a microcontroller.

52. A reconfigurable electrochemical biosensor adapted for performing a plurality of measurement techniques.

53. The reconfigurable electrochemical biosensor of Paragraph 52, wherein said plurality of measurement techniques are implemented without redundancy of circuit components for the plurality of measurement techniques.

54. The reconfigurable electrochemical biosensor of any one of Paragraphs 52 and 53, wherein said plurality of measurement techniques comprise amperometric measurements, potentiometric measurements, and impedance spectroscopy.

55. The reconfigurable electrochemical biosensor of any one of Paragraphs 52-54, wherein said smartphone comprises a Google's Project Ara™ smartphone.

56. The reconfigurable electrochemical biosensor of any one of Paragraphs 52-55, wherein said reconfigurable electrochemical biosensor comprises a potentiostat adapted to perform a plurality of electrochemical detection techniques.

57. The reconfigurable electrochemical biosensor of any one of Paragraphs 52-56, further comprising a connection port adapted for high-speed communication with said smartphone or wearable device.

58. The reconfigurable electrochemical biosensor of any one of Paragraphs 52-57, further comprising a testing port adapted to interface with a plurality of external test strips or electrodes.

59. The reconfigurable electrochemical biosensor of any one of Paragraphs 52-58, wherein said plurality of measurement techniques is selected from the group consisting of cyclic voltammetry, chronoampermetry, square wave voltammetry and differential pulse voltammetry.

60. The reconfigurable electrochemical biosensor of any one of Paragraphs 52-59, wherein said measurement techniques are adapted to perform an analysis selected from the group consisting of glucose testing, measuring pH, health and wellness monitoring, monitoring chronic illnesses, monitoring Cystic Fibrosis, monitoring inflammation, assessing food or water safety, detection of heavy metal or *salmonella* in the environment or produce, daily health tracking, measuring cholesterol or hydration levels, detecting an infectious or pathogenic agent, detecting malaria, detecting HIV, detecting HCV, and detecting TB.

61. The reconfigurable electrochemical biosensor of any one of Paragraphs 52-60, further comprising two working electrodes (WE) with each channel having independently configurable gain.

62. The reconfigurable electrochemical biosensor of any one of Paragraphs 52-61, further comprising a digital to analog converter and an analog to digital converter.

63. The reconfigurable electrochemical biosensor of any one of Paragraphs 52-62, further comprising a microcontroller.

64. A method of performing a biological analysis comprising performing said biological analysis on a subject or a biological sample obtained from a subject using a smartphone or wearable device of any one of Paragraphs 40-51 or a reconfigurable electrochemical biosensor of any one of Paragraphs 52-63.

65. The method of Paragraph 64, wherein said biological analysis is performed by placing said smartphone or wearable device of any one of Paragraphs 40-51 or a reconfigurable electrochemical biosensor of any one of Paragraphs 52-63 in contact with a portion of said subject's body.

66. A system for performing electrochemical sensing tests on a subject's body, comprising: a portable electronic platform; and a reconfigurable electrochemical biosensing circuit configured to perform a plurality of measurement techniques in a plurality of modes comprising an amperometric mode to perform a amperometric measurement, a potentiometric mode to perform a potentiometric measurement, and electrochemical impedance spectroscopy (EIS) mode to perform EIS on the body.

67. The system of Paragraph 66, further comprising a disposable test strip configured to connect to the reconfigurable electrochemical biosensing circuit.

68. The system of any one of Paragraphs 66-67, wherein the reconfigurable electrochemical biosensing circuit comprises a potentiostat.

69. The system of any one of Paragraphs 66-68, wherein the reconfigurable electrochemical biosensing circuit comprises two working electrodes and two resistive feedback transimpedance amplifiers (TIAs) connected to a respective working electrode, and wherein each TIA has an independently adjustable gain and bandwidth.

70. The system of any one of Paragraphs 66-69, wherein the two working electrodes are configured to be run simultaneously.

71. The system of any one of Paragraphs 66-70, wherein the reconfigurable electrochemical biosensing circuit further comprises a reference electrode and a counter electrode to set a potential for the reconfigurable electrochemical biosensing circuit.

72. The system of any one of Paragraphs 66-71, wherein the reconfigurable electrochemical biosensing circuit further comprises an input buffer connected to the reference electrode in the amperometric mode, and wherein the input buffer is configured as a high impedance input for an op-amp in the potentiometric mode.

73. The system of any one of Paragraphs 66-72, wherein the reference electrode is configured to be floating in the EIS mode.

74. The system of any one of Paragraphs 66-73, wherein a first two-electrode sensor is attached between the counter electrode and a first one of the working electrodes.

75. The system of any one of Paragraphs 66-74, wherein a second two-electrode sensor is attached between the counter electrode and a second one of the working electrodes.

76. The system of any one of Paragraphs 66-75, wherein the portable electronic platform comprises smartphone, smartwatch, personal digital assistant (PDA), tablet computer, textile including electronic components or any wearable technology, home appliance, vehicle or autonomous vehicle.

DETAILED DESCRIPTION OF THE CERTAIN INVENTIVE EMBODIMENTS

Figure 1:
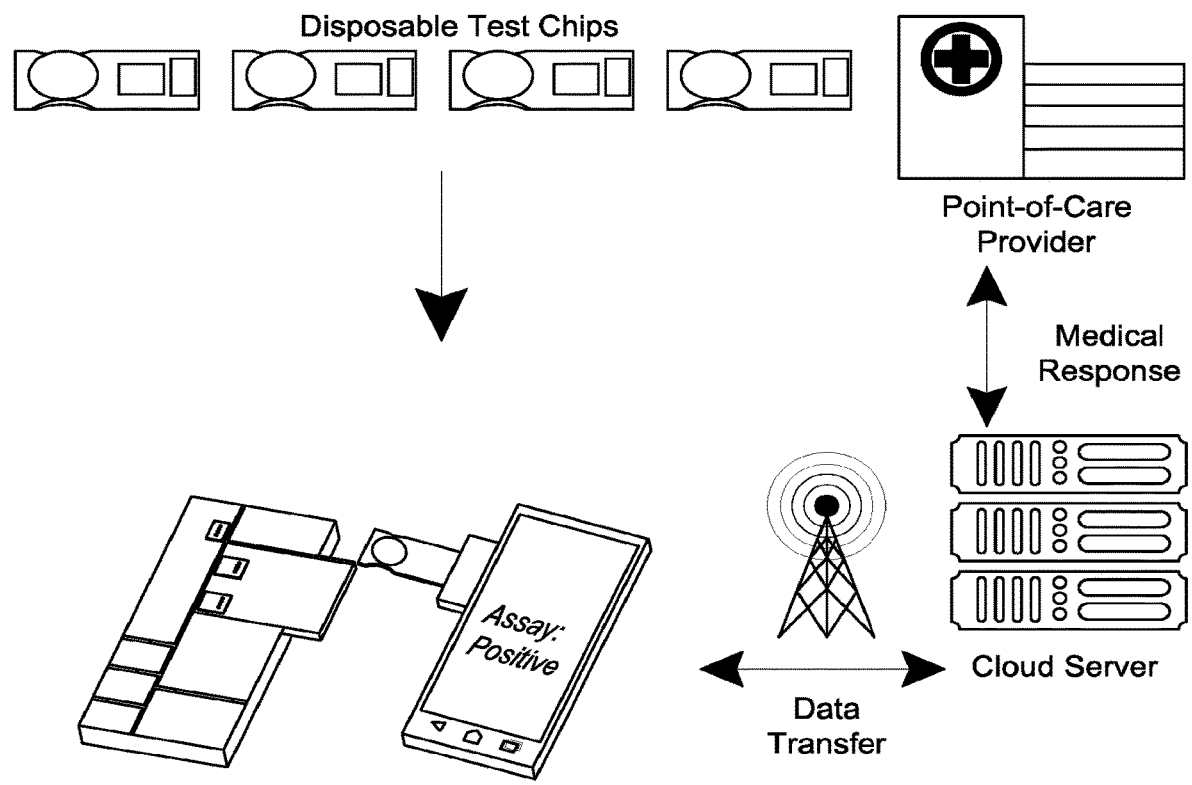
FIG. 1: Complete electrochemical biosensor platform with disposable electrodes, biosensor module, and modular mobile device such as Google ATAP's Project Ara™.

Some embodiments disclosed herein relate to a design for an electrochemical biosensor module for direct integration into a smartphone, wearable device, textile, home appliance, vehicle, autonomous vehicle or system through the use of a novel reconfigurable bipotentiostat capable of supporting an extended range of techniques while minimizing the number of required components. In some embodiments, the system comprises the following components:

1) a disposable test chip, the type of which depends on the application,
2) the reconfigurable potentiostat sensing module, and
3) the mobile platform.

Some embodiments described herein relate to a module in conformance with the Project Ara Module Developers Kit (MDK) that enables point-of-care (POC) diagnostic applications, thereby improving the convenience and speed of medical diagnoses. The mobile platform used in some of the embodiments described herein is Google ATAP's Project Ara (Spiral 1 prototype) modular smartphone, which allows the user to swap out different components easily and customize the phone's hardware. This platform facilitates biosensor integration because of its open and high-speed interface as well as its modularity that enables the smartphone to have bio-sensing, amongst many other, capabilities. However, the platform is not limited to any particular device and can be any device or material, even textile, that can include the reconfigurable potentiostat.

Some embodiments relate to a module that comprises a potentiostat, which is a device capable of running a wide range of electrochemical detection techniques, modified to allow a high degree of reconfigurability in space/power constrained mobile environments. In some embodiments, the module is capable of high-speed communication with its host device (smartphone or wearable) and has the flexibility to interface with many external test chips or electrodes functionalized for a specific task, much like the test strips made for glucose meters. For example, in some embodiments, with this module and external test chips, the user can run molecular detection tests, using amperometric, potentiometric, and impedance spectroscopy techniques, away from the hospital or centralized laboratory all with their mobile device.

While there already exists external bio-sensing peripherals for smartphones that interface via the I/O ports on the phone (audio port, USB, etc.), such devices are not currently developed to integrate directly into the phone itself as part of the internal hardware. Furthermore, while some health related sensors have already been extensively integrated into wearable technology such as photoplethsymograms and electrocardiogram machines, such sensors are not used specifically for molecular detection of biomarkers.

In the existing art, portable and miniature potentiostat devices are only designed for a single family of electrochemical techniques. However, in some embodiments described herein, the potentiostat circuit design itself has digital reconfigurablilty to be able to change its mode of testing without the addition of more high power components. For example, in some embodiments, it can run in three different modes (amperometric, potentiometric, and impedance spectroscopy), all with the same components.

In some embodiments, the devices described herein may perform analyses such as pH measurements and glucose assays. In some embodiments, additional sensors may be added and, if desired, the costs of making the devices may be reduced and the form factor may be further improved. In some embodiments, the devices described herein may be specialized, portable, and practical medical devices well-positioned to be the first line of defense in the future of healthcare.

Some embodiments relate to a reconfigurable and multi-technique electrochemical biosensor for integration into smartphone and wearable technologies. In some embodiments, the biosensor may be a small electronic module that is added as dedicated hardware to a smartphone, wearable device or material, such as textile, in order to enable portable molecular detection of biological or environmental samples. In some embodiments, the device may provide a portable platform for Point-of-Care health monitoring when integrated into mobile technology. In some embodiments, the module may comprise a potentiostat capable of running a wide range of electrochemical detection techniques, modified to allow reconfigurability in space/power constrained mobile environments. In some embodiments, the reconfigurable biosensor may be capable of high-speed communication with its host device (smartphone or wearable) and may have the flexibility to interface with external test chips or electrodes functionalized for a specific task, much like the test strips made for glucose meters. In some embodiments, with this module and external test chips, the user can run molecular detection tests, using amperometric, potentiometric, and impedance spectroscopy techniques, away from the hospital or centralized laboratory all with their mobile device.

While there already exists external biosensing peripherals for smartphones that interface via the I/O ports on the phone (audio port, USB, Lightening, etc.), such devices are not currently developed integrate directly into the phone itself as part of the internal hardware. Furthermore, while some health related sensors have already been extensively integrated into wearable technology such as photoplethsymograms (PPG) and electrocardiogram machines, such sensors are not used specifically for molecular detection of biomarkers. Some embodiments of the devices described herein provide a miniature form factor and dedicated electronics for seamless integration, allowing for such molecular detection functionality to be added into a smartphone or wearable increasing convenience and practicality of testing.

Furthermore, existing portable and miniature potentiostat devices (generally lower cost and more easily miniaturized than other sensing modalities) are only designed for a single family of electrochemical techniques. In some embodiments described herein, the biosensor, such as a potentiostat circuit or other biosensor, has digital reconfigurablilty to be able to change its mode of testing without the addition of more high power components. For example, in some embodiments, the biosensor or potentiostat can run in three different modes (amperometric, potentiometric, and impedance spectroscopy) all with the same components.

In some embodiments, the present devices provide advantages over commercially available glucose meters that act as peripherals to smartphones, e.g. iBGStar® Glucose Meter, Dario® Smart Meter, and OneTouch Verio® Synce Meter or devices such as those described in the following U.S. patents or published patent applications: U.S. Pat. No. 8,947,656 B2, U.S. Pat. No. 8,923,918 B2, US 2014/0012511 A1, US 2013/0012796 A1, US 2014/0099237 A1, US 2014/0170761 A1. While all these leverage the smartphone, they are still external to the mobile device and most only deal with the sensing of glucose rather than multiple biomarkers.

There are also devices that have been published which are portable potentiostats that use the smartphone such as those described in the following references, each of which is incorporated herein by reference in its entirety:
[1] A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," PNAS, vol. 111, no. 33, pp. 11984-11989, August 2014.
[2] C. Ionescu, P. Svasta, C. Tamas, C. Bala, and L. Rotariu, "Portable measuring and display unit for electrochemical sensors," in Design and Technology in Electronic Packaging (SIITME), 2010 IEEE 16th International Symposium for, 2010, pp. 215-218.
[3] P. B. Lillehoj, M.-C. Huang, N. Truong, and C.-M. Ho, "Rapid electrochemical detection on a mobile phone," Lab Chip, vol. 13, no. 15, pp. 2950-2955, July 2013.

Further embodiments are described below.

Figure 2:
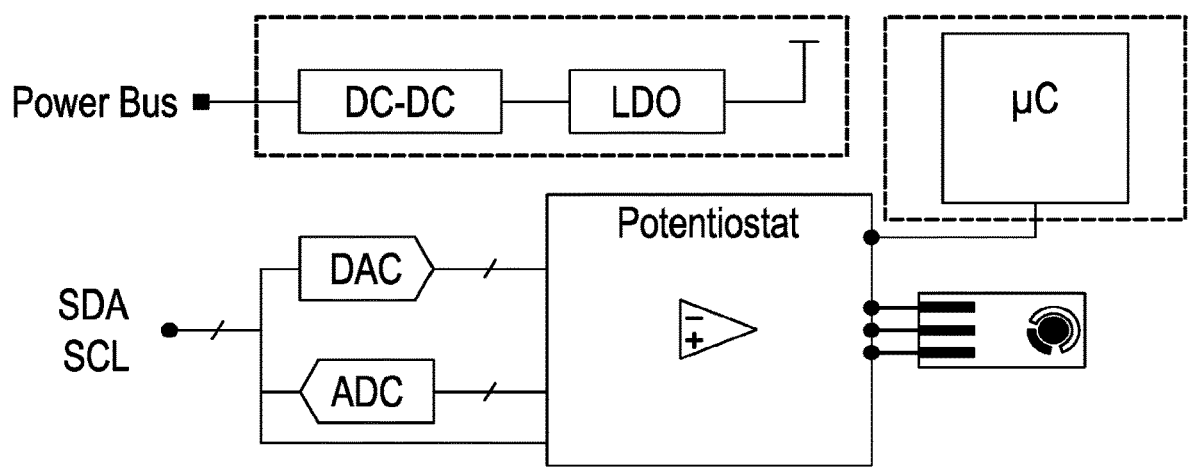
FIG. 2: Block diagram of the biosensing module.
Figure 3:
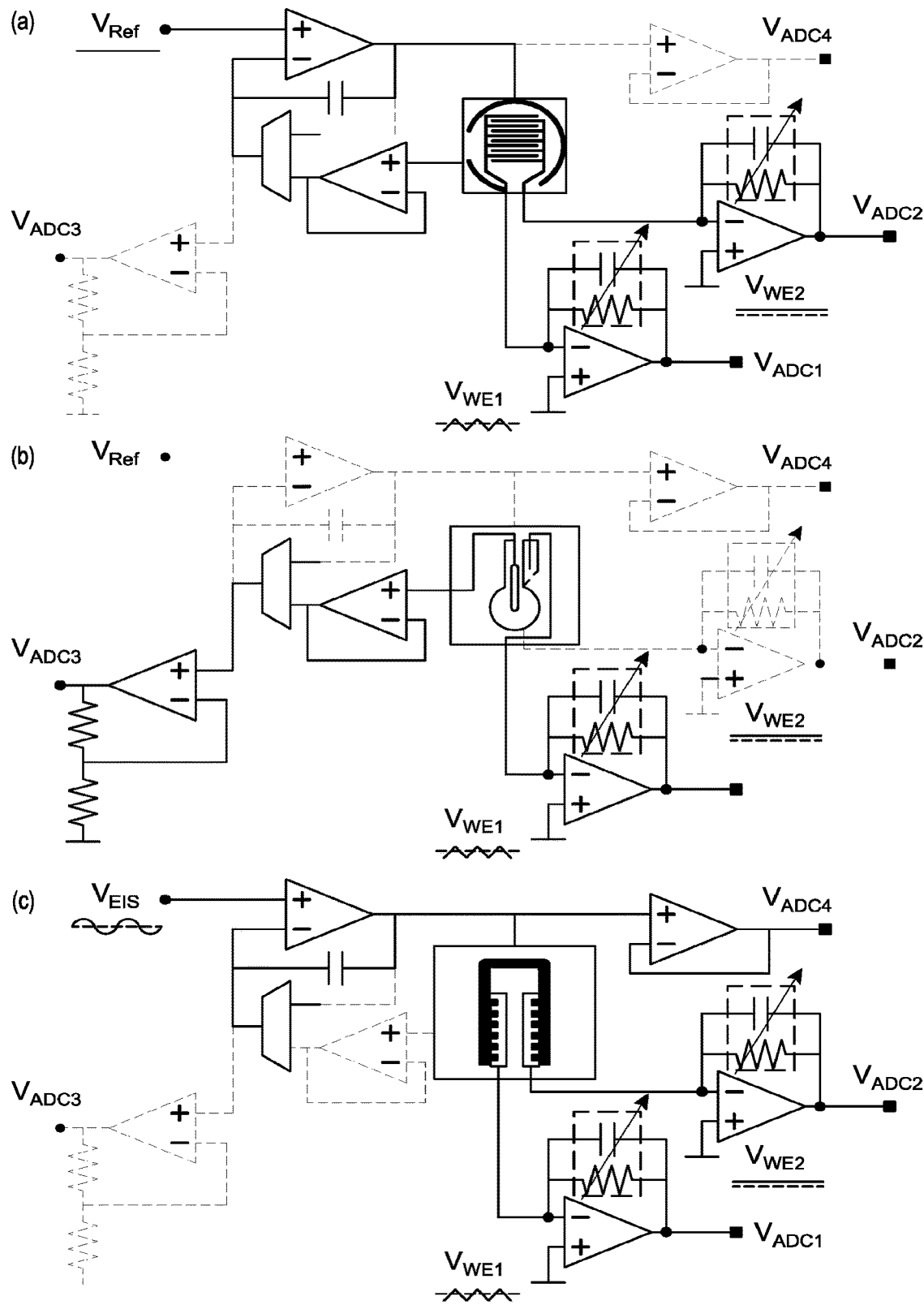
FIG. 3: Schematic of a) Amperometric, b) potentiometric, and c) impedance spectroscopy modes.

Once integrated with a host device (FIG. 1), in some embodiments, the module may be combined with test chips inserted into its connector, a biological sample is applied to the chip, and the user can run a test via an application that controls the module. The overall design of an exemplary module is as shown in the block diagram of FIG. 2. An onboard microcontroller handles communication with the specific high-speed bus of the host device and, using the specific parameters set by the user application, controls the potentiostat to run electrochemical techniques. Depending on the test, the potentiostat (FIG. 3) can then configure itself to properly apply the appropriate signals to the chip and make measurements on the biological sample. The configurability of the potentiostat means that depending on the specific test chip used and technique desired it can apply different voltage waveforms to the test chips and measure current, voltage, or impedance spectrum.

Figure 4:
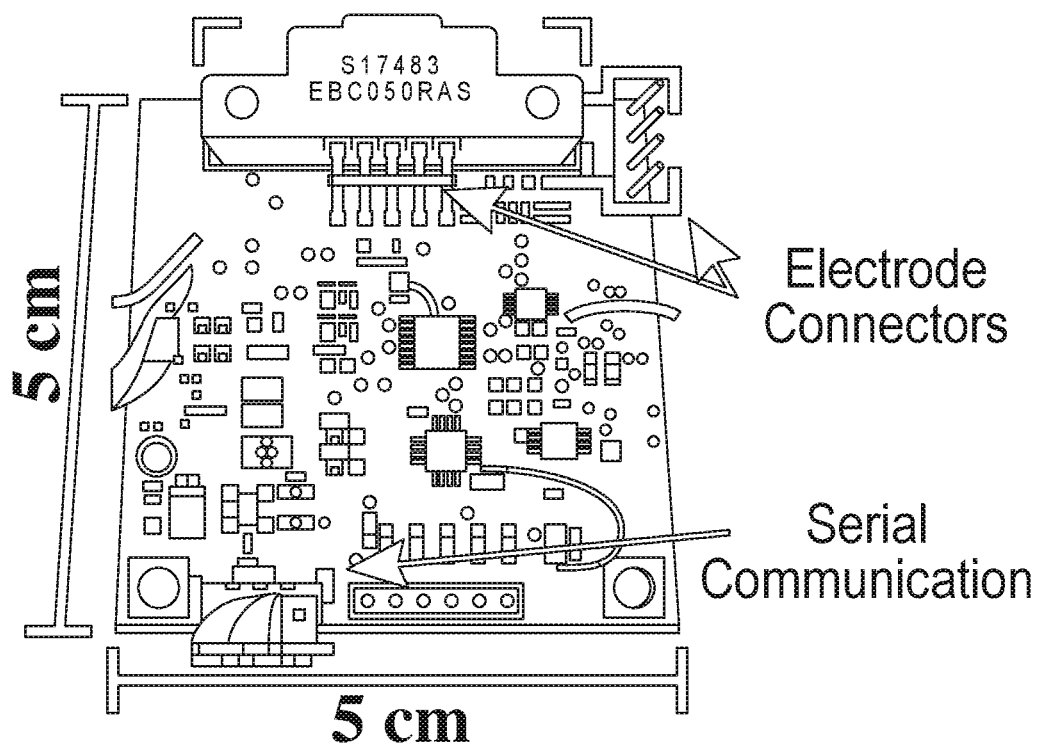
FIG. 4: Photograph of the PCB prototype biosensor module.
Figure 5:
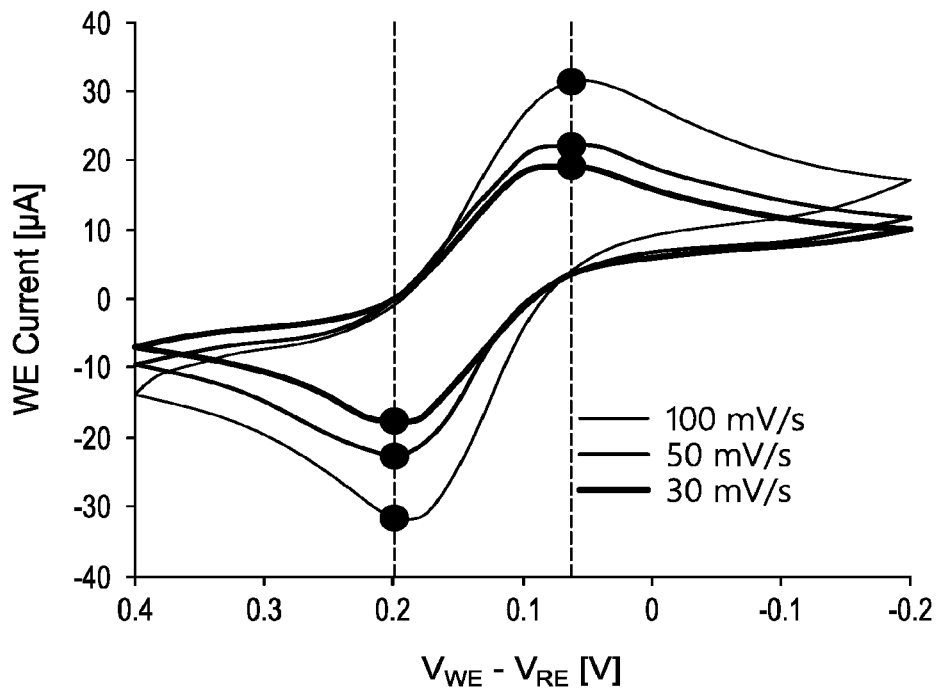
FIG. 5: a) Voltammograms at different scan rates, b) the anodic current peak plotted against scan rate measured by both the module and CHI.
Figure 5:
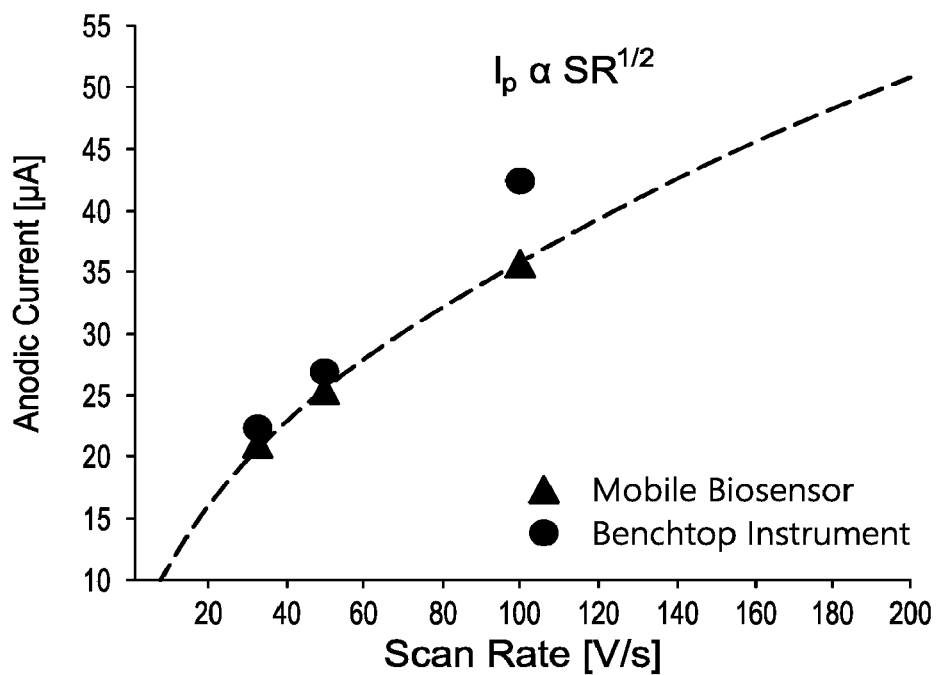

A photograph of an exemplary PCB and its performance are shown in the below and in (FIG. 4). As demonstrated in FIG. 5-7, which show measurements made by the platform, the device can run amperometric and potentiometric techniques for different biosensing tests (Glucose and pH tests, along with proof-of-concept cyclic voltammetry measurements). In some embodiments, the device may be adapted to a smaller form factor. In some embodiments, the circuit may be integrated with a modular smartphone development board and used to perform additional biomarker detection assays.

In some embodiments, the devices described herein may be used in mHealth and point-of-care devices market. Many mobile phone and wearable technology companies have begun to integrate medically relevant sensors such as accelerometers and PPGs into their products, yet no integrated molecular sensor has been developed. In some embodiments, the devices described herein enable at-home or remote diagnostic tests all with only a mobile device and inexpensive disposable test chip. Since this frequent, convenient, and early testing could reduce medical costs and improve patient health, there would be a large market for such a device. Examples of assays include: glucose testing for diabetics, health and wellness monitoring for chronically ill patients, such as those with Cystic Fibrosis or varying types of inflammation, food and water safety, e.g., detection of heavy metal or *salmonella* in the environment or produce, daily health tracking such as measuring cholesterol and hydration levels, and infectious disease testing for Malaria, human immunodeficiency virus (HIV), hepatitis C (HCV), or tuberculosis (TB).

The leading cause of death and disability in the United States is from chronic illnesses such as heart disease, stroke, cancer, and diabetes, which are the most commonly diagnosed and also the most expensive to treat (B. W. Ward, J. S. Schiller, and R. A. Goodman, "Multiple Chronic Conditions Among US Adults: A 2012 Update," *Prev. Chronic. Dis.*, vol. 11, April 2014). One of the main factors for this occurrence is the current heavy reliance on periodic hospital checkups that can increase facilities costs and reduce affordability, especially if frequent assessment or continuous monitoring is required.

Fortunately, recent advances in portable electronics, allow for the design of mobile health (mHealth) technology to continuously monitor patients at the point-of-care (POC). While current and next generation mobile devices already boast an impressive array of integrated health oriented sensors, such as electrocardiogram (ECG) and photoplethsymogram (PPG), there remains a lack of molecular sensors to detect biomarkers. These biomolecular sensors, which can enable applications such as remote or at-home diagnosis of infection, monitoring treatment progression, hydration and fatigue tracking during exercise, and testing food and water safety, offer a much more complete and diagnostically relevant picture of the user's health. While several add-on biosensing modules for mobile phones have been developed that leverage intrinsic hardware (e.g., the camera or audio port), these devices are still external to the phone making them more burdensome to manage and transport than a fully integrated solution, dissuading frequent and daily use (A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," *Proc. Natl. Acad. Sci.*, vol. 111, no. 33, pp. 11984-11989, August 2014; P. B. Lillehoj, M.-C. Huang, N. Truong, and C.-M. Ho, "Rapid electrochemical detection on a mobile phone," *Lab. Chip*, vol. 13, no. 15, pp. 2950-2955, July 2013; A. Sun, T. Wambach, A. G. Venkatesh, and D. A. Hall, "A low-cost smartphone-based electrochemical biosensor for point-of-care diagnostics," in 2014 IEEE Biomedical Circuits and Systems Conference (BioCAS), 2014, pp. 312-315; V. Oncescu, D. O'Dell, and D. Erickson, "Smartphone based health accessory for colorimetric detection of biomarkers in sweat and saliva," Lab. Chip, vol. 13, no. 16, pp. 3232-3238, July 2013; V. Oncescu, M. Mancuso, and D. Erickson, "Cholesterol testing on a smartphone," *Lab. Chip*, vol. 14, no. 4, pp. 759-763, Jan. 2014; M. Zangheri, L. Cevenini, L. Anfossi, C. Baggiani, P. Simoni, F. Di Nardo, and A. Roda, "A simple and compact smartphone accessory for quantitative chemiluminescence-based lateral flow immunoassay for salivary cortisol detection," Biosens. Bioelectron., vol. 64, pp. 63-68, February 2015; S. K. J. Ludwig, H. Zhu, S. Phillips, A. Shiledar, S. Feng, D. Tseng, L. A. van Ginkel, M. W. F. Nielen, and A. Ozcan, "Cellphone-based detection platform for rbST biomarker analysis in milk extracts using a microsphere fluorescence immunoassay," *Anal. Bioanal. Chem.*, vol. 406, no. 27, pp. 6857-6866, June 2014). By integrating biosensors into a smartphone, smartwatch, smartphone, smartwatch, personal digital assistant (PDA), tablet computer, material, such as textile, including electronic components, any wearable technology or any other type of platform mentioned in this document, and leveraging the scalability, cost-effectiveness, and accuracy of electrochemical biosensing, which led to the success of glucose meter, one can develop much more convenient and seamless mHealth applications that can promote adherence to frequent or continuous testing.

To this end, we describe the design of an electrochemical biosensor module for direct integration into a platform through the use of a novel reconfigurable bipotentiostat capable of supporting an extended range of techniques while minimizing the number of required components. In an exemplary embodiment, the entire system (FIG. 1) has three main components: 1) a disposable test chip, the type of which depends on the application, 2) the reconfigurable potentiostat sensing module, and 3) the mobile platform.

The mobile platform used can be Google ATAP's Project Ara (Spiral 1 prototype) or similar modular smartphone (FIG. 1), which allows the user to swap out different components easily and customize the phone's hardware. This platform can be effective for biosensor integration because of its open and high-speed interface as well as its modularity that enables the smartphone to have biosensing, amongst many other, capabilities.

Design of an Exemplary Module

The module (FIG. 2) can include a potentiostat surrounded by a 4-channel 12-bit digital-to-analog converter (DAC) and analog-to-digital converter (ADC) as well as a low-power microcontroller to handle interfacing with the smartphone or wearable. To enable a large set of possible mHealth applications, the potentiostat must be able to run multiple types of techniques, which require different sensing modes and additional circuitry. However, space and power are highly constrained resources on a mobile device. Therefore, in order to reduce the area and, more importantly when moving to an integrated circuit implementation, the power, a single reconfigurable design, rather than three different sets of potentiostat circuits, is used that repurposes components from one mode to the next while maintaining performance across different techniques. Hence, the potentiostat (FIG. 2) is designed to be able to change automatically between three different modes: 1) amperometric, 2) potentiometric, and 3) impedance spectroscopy.

This potentiostat has two working electrodes (WE) with each channel having independently configurable gain (10 k$\Omega$, 100 k$\Omega$, and 1 M$\Omega$) and bandwidth (adding any combination of a 1, 10, and 100 nF capacitor in parallel). This functionality enables two tests to be run in parallel simultaneously on the same sample, allowing one to be a control to compensate for factors such as temperature variation or background signal. Alternatively, the electrodes can be used together for redox cycling with an interdigitated electrode in order to chemically amplify the signal to provide higher sensitivity, particularly when dealing with micro- and nano-scale sensors (J. Das, K. Jo, J. W. Lee, and H. Yang, "Electrochemical Immunosensor Using p-Aminophenol Redox Cycling by Hydrazine Combined with a Low Background Current," Anal. Chem., vol. 79, no. 7, pp. 2790-2796, April 2007). Each of these modes and their requirements are explained in the following sections.

A. Amperometric Mode

In some embodiments, in amperometry, a voltage signal is applied to the sensor between the reference electrode (RE) and the WE, with the counter electrode (CE) supplying the current to set the solution potential. This voltage waveform generates a current signal in the solution that is measured at the WE. These set of techniques are the most widely used and include cyclic voltammetry (CV), chronoampermetry (CA), square wave voltammetry (SWV), and differential pulse voltammetry (DPV). The simplified schematic of this mode is shown in FIG. 3(a). Strategically placed multiplexers allow the circuit to be switched at nodes that do not affect performance.

A summary of the specifications used for some embodiments are shown in Table 1. Since the sensitivity of these measurements depends on how accurately current can be measured, the most important design considerations for this mode are the input-referred noise, which was measured with about 100 kOhm gain and about 1 kHz bandwidth, and the input bias current of the transimpedance amplifier (TIA). Since low leakage multiplexors (about 5 pA) for selecting the gain and bandwidth are used and the number of mux inputs connected to the inverting node are minimized, the overall input leakage for the TIA is dominated by the input bias current of the op-amp. Hence, we can measure currents in the sub-nA range, sufficient for most applications which tend to be anywhere from a bidirectional about 100 $\mu$A to about 1 pA, depending on the type and size of the sensor used. Furthermore, the input bias current of the RE circuitry must be minimized in order to reduce the IR error of the applied voltage, which affects the accuracy of the voltage applied between the electrodes. By using a very low input bias op-amp, this design can achieve an RE leakage of about 200 fA, which, with a typical solution resistance of about 100$\Omega$, contributes about 100 nV error which is negligible.

TABLE 1

| Specifications for Each Mode | |
|---|---|
| Amperometric | |
| Sensitivity | <1 nA |
| Dynamic Range | 60 dB (1 nA-1 $\mu$A) |
| Input-Referred Noise | 216 pA$_{RMS}$ (0.1 Hz-1 kHz) |
| Input Bias Current (RE) | ~200 fA |
| Input Bias Current (WE) | 170 pA |
| Potentiometric | |
| Leakage Current | ~200 fA |
| Input Impedance | ~20 T$\Omega$ |
| Input-Referred Noise | 1.06 $\mu$V$_{RMS}$ (0.1-10 Hz) |
| Dynamic Range | 66 dB (1 mV-2 V) |
| Impedance Spectroscopy | |
| Bandwidth | 0.1 Hz-100 kHz |
| Maximum AC Current | ±5 mA |

B. Potentiometric Mode

In the potentiometric mode shown in FIG. 3(b), the voltage generated between two electrodes in a solution is measured. Typically, an ion-selective electrode (ISE) is used, often to measure pH or specific ion concentrations. These electrodes have very large resistances, in the 100 MΩ range, and required circuitry with an input bias current of less than 1 pA (this design is 200 fA) to ensure that measurement error is less than 1%. In some embodiments, without adding a new set of components, the input buffer used for RE in the amperometric mode can be switched into the signal path for use as a high impedance input. This is the same path used for the RE in ampereometric modes.

C. Impedance Spectroscopy

In the electrochemical impedance spectroscopy (EIS) mode, a small-signal voltage of varying frequency is applied between the RE and WE in the test solution as shown in FIG. 3(c). The phase and amplitude of the resulting current signal is used to determine the complex impedance of the solution across different frequencies, typically in the range of about 0.1 Hz to about 100 kHz, however the frequency is not limited thereto. Known test impedances can be connected in between the two electrodes in order to characterize the phase shift in the signal path and compensate the channel accordingly. Due to the high frequency nature of the input and output signals, the hardware is required to be able to operate at high frequencies, which contrasts greatly with the low frequency signals of the previous two modes. This requires further bandwidth adjustments for the control circuitry as well as the TIA.

D. Communication Interface

Timing is a critical issue especially for EIS where an exact phase shift must be determined. Hence, precise polling of the ADCs and DACs can be accomplished by adding a microcontroller to mediate between the potentiostat and the mobile platform. In addition to achieving proper timing, the microcontroller also allows one to easily adapt this module to fit any standard serial communication protocol, further increasing its utility.

Chemical Verification

A 5×5 cm prototype of the device, shown in FIG. 4, was tested to verify the functionality and performance. With smaller component packages and more routing layers on the PCB, there is no reason that this cannot be further miniaturized to meet the size requirements.

A. Cyclic Voltammetry Comparison

Cyclic voltammetry experiments were conducted with an equal mixture of potassium ferro/ferri-cyanide ($K_4[Fe(CN)_6]$)/($K_3[Fe(CN)_6]$) from Spectrum (P1286, P1296) in a phosphate buffer solution (PBS) of 150 mM potassium phosphate monobasic from Fischer Scientific (P285-500) and potassium phosphate dibasic from EMD Millipore (PX1570-1). 1 mM samples of this solution were applied to gold screen printed electrodes (SPEs) from DropSens. To ensure that we could capture standard voltamograms, cyclic voltammetry measurements, sweeping from −200 mV to 400 mV while varying the scan rate, were made with both the module biosensor and a benchtop potentiostat (CHI 750E) from CH Instruments (FIG. 5a). The analyzed results show that the characteristic anodic (200 mV) and cathodic (60 mV) peak voltages match with that of the CHI. Furthermore, the relationship between the scan rate and peak current (FIG. 5b) fits the Randles-Sevcik equation.

B. pH Measurements

Figure 6:
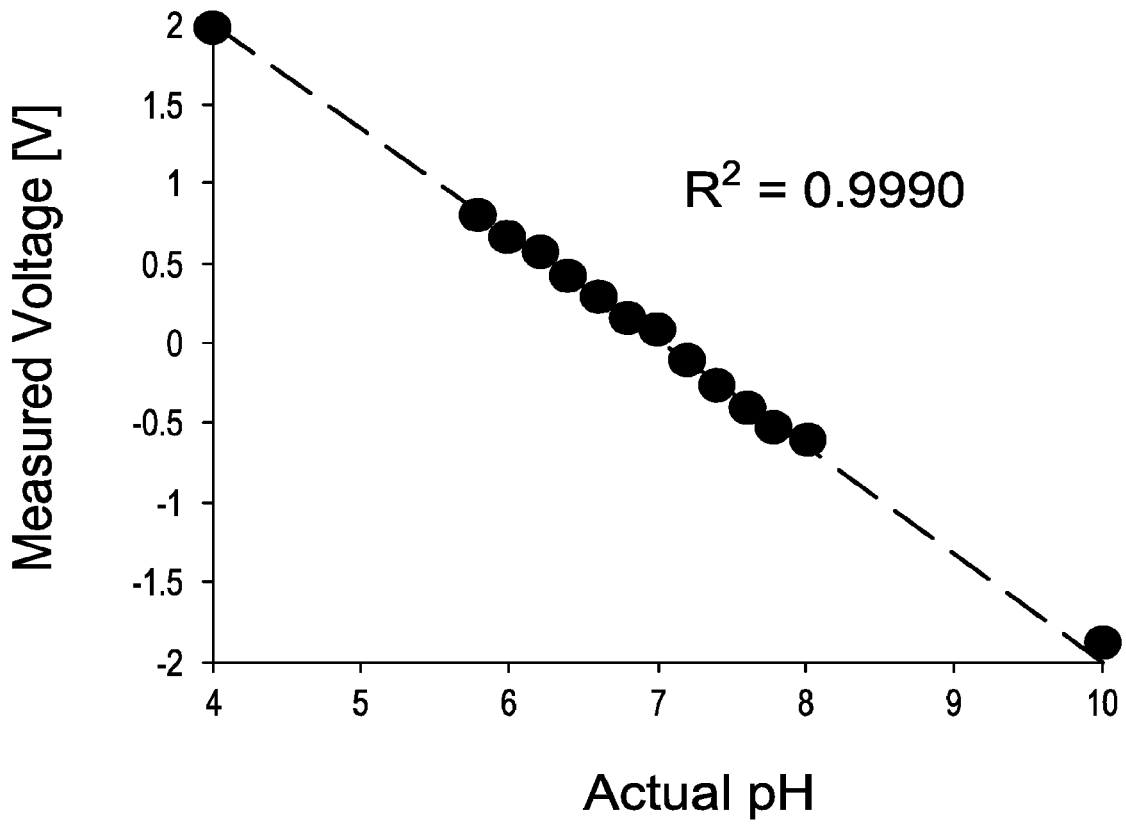
FIG. 6: pH calibration curve with fitted line.
Figure 7:
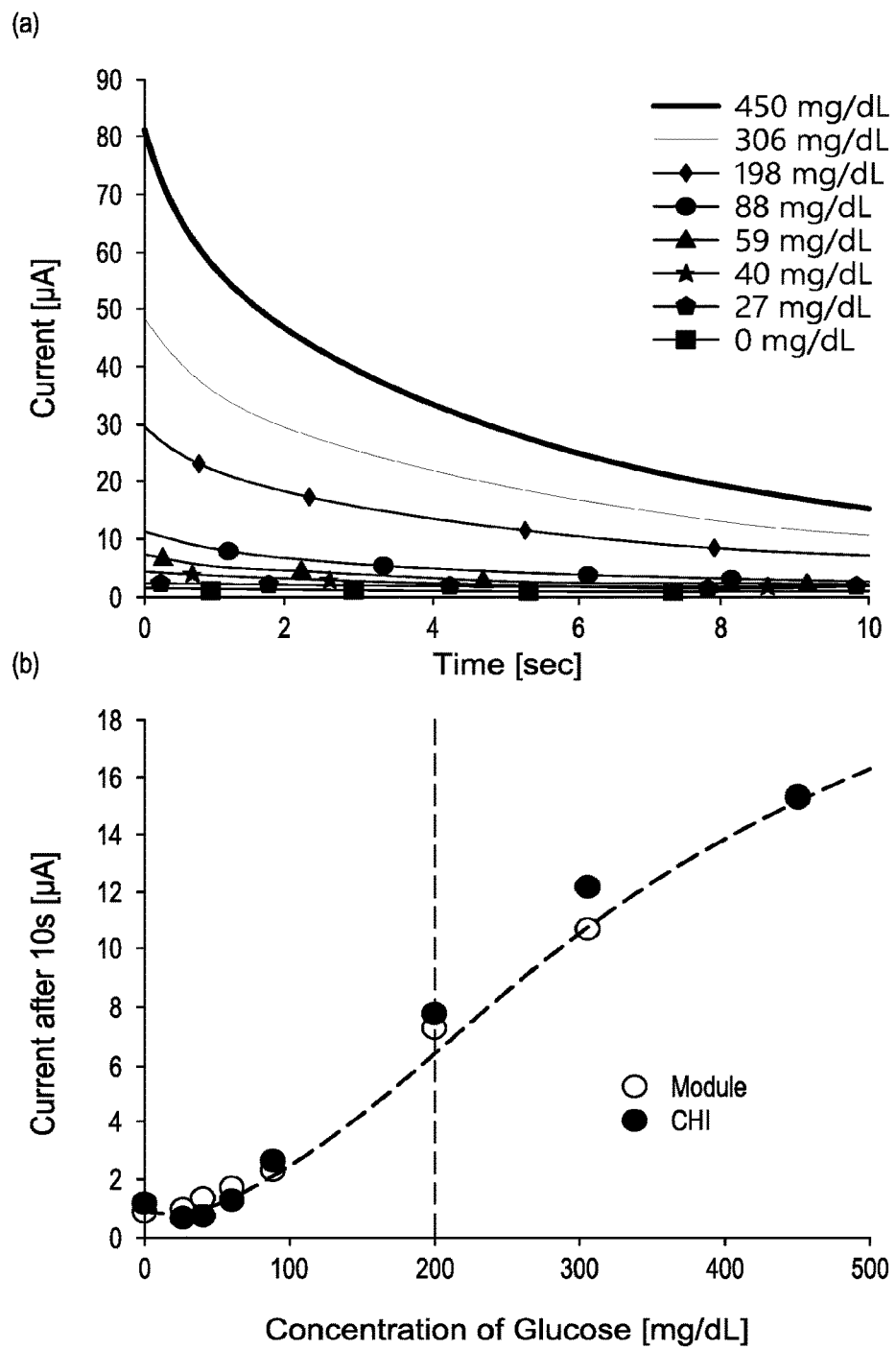
FIG. 7: a) Chronoamperometry curves for glucose measured by the sensing module and b) calibration curves for both the biosensor and CHI with the positive and negative diagnosis ranges annotated.

For pH measurements, standard pH buffers from Thermo Scientific (910104, 910107, and 910110) were used as well as prepared phosphate buffers adjusted to specific values ranging from pH 4-10. All measurements were taken with an Oakton pH Probe (EW-35811-74). These buffers were measured with the biosensor module in potentiometric mode and verified with a table top pH meter (Orion Star A211). The results, as seen in FIG. 6, show a strong linear relationship between the measured voltage and actual pH, as expected.

C. Glucose Measurements

For Glucose experiments, PBS was spiked with various concentrations of Dextrose from Marcon (4912-12) to create the test solutions. Commercial glucose test strips (True Test Blood Glucose Strips) based on Glucose dehydrogenase-PQQ (GDH) were applied with the various test solutions (27-450 mg/dL) and measured with chronoamperometry (0.5 V step for 10 seconds) with both the CHI and the biosensor module. The results (FIG. 7) show that the measured currents (taken after 10 seconds) for each concentration measured by both instruments follow the same trend. The calibration curve demonstrates that the assay is in the correct region to be able to diagnose or monitor diabetes (positive above 200 mg/dL according to the American Diabetes Association).

Need for Electrochemical Biosensors

Chronic illnesses, such as heart disease, stroke, cancer, and diabetes, are not only the leading cause of death and disability in the US, but also the most commonly diagnosed and expensive health issues to treat (B. W. Ward, J. S. Schiller, and R. A. Goodman, "Multiple Chronic Conditions Among US Adults: A 2012 Update," *Prev. Chronic. Dis.*, vol. 11, April 2014). One of the many reasons for these phenomena is the heavy reliance on periodic hospital check-ups as the sole mechanism to determine one's well-being. While remote and at-home testing is a promising solution to help alleviate this burden on the healthcare system and potentially improve one's health, most medical diagnostic equipment today is confined to centralized laboratories and hospitals. Furthermore, this equipment is too expensive and bulky for direct point-of-care (POC) use.

Fortunately, recent advances in portable electronics and sensor miniaturization have allowed for the development and proliferation of mobile health (mHealth) technologies that can continuously monitor patients at the POC, away from traditional hospital settings. Many mobile devices have fitness oriented sensors built-in, such as accelerometers for tracking physical activity, electrocardiograms (ECG) to record the electrical signals of the heart, and photoplethysmogram (PPG) to determine heart rate as well as the blood oxygenation level. Unfortunately, these sensors offer limited medically actionable data, especially for those with chronic diseases. Biomolecular sensors, on the other hand, that measure the constituents of biological samples (e.g., blood, urine, saliva, etc.) provide a much more complete and medically relevant picture of the user's health. Such sensors could be used for at-home diagnosis of infection, monitoring of treatment progression (A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," *Proc. Natl. Acad. Sci.*, vol. 111, no. 33, pp. 11984-11989, August 2014; P. B. Lillehoj, M.-C. Huang, N. Truong, and C.-M. Ho, "Rapid electrochemical detection on a mobile phone," *Lab. Chip*, vol. 13, no. 15, pp. 2950-2955, July 2013; B. Berg, B. Cortazar, D. Tseng, H. Ozkan, S. Feng, Q. Wei, R. Y.-L. Chan, J. Burbano, Q. Farooqui, M. Lewinski, D. Di Carlo, 0. B. Garner, and A. Ozcan, "Cellphone-Based Hand-Held Microplate Reader for Point-of-Care Testing of Enzyme-Linked Immunosorbent Assays," *ACS Nano*, vol. 9, no. 8, pp.

7857-7866, August 2015), hydration and fatigue tracking during exercise (V. Oncescu, D. O'Dell, and D. Erickson, "Smartphone based health accessory for colorimetric detection of biomarkers in sweat and saliva," *Lab. Chip*, vol. 13, no. 16, pp. 3232-3238, July 2013), and testing food and water safety (A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," *Proc. Natl. Acad. Sci.*, vol. 111, no. 33, pp. 11984-11989, August 2014; X. Wang, M. R. Gartia, J. Jiang, T.-W. Chang, J. Qian, Y. Liu, X. Liu, and G. L. Liu, "Audio jack based miniaturized mobile phone electrochemical sensing platform," *Sens. Actuators B Chem.*, vol. 209, pp. 677-685, March 2015; C. Ionescu, P. Svasta, C. Tamas, C. Bala, and L. Rotariu, "Portable measuring and display unit for electrochemical sensors," in *Design and Technology in Electronic Packaging (SIITME), 2010 IEEE 16th International Symposium for,* 2010, pp. 215-218; S. K. J. Ludwig, C. Tokarski, S. N. Lang, L. A. van Ginkel, H. Zhu, A. Ozcan, and M. W. F. Nielen, "Calling Biomarkers in Milk Using a Protein Microarray on Your Smartphone," *PLoS ONE*, vol. 10, no. 8, p. e0134360, August 2015; S. K. J. Ludwig, H. Zhu, S. Phillips, A. Shiledar, S. Feng, D. Tseng, L. A. van Ginkel, M. W. F. Nielen, and A. Ozcan, "Cellphone-based detection platform for rbST biomarker analysis in milk extracts using a microsphere fluorescence immunoassay," *Anal. Bioanal. Chem.*, vol. 406, no. 27, pp. 6857-6866, June 2014).

While several add-on biosensing modules for mobile phones have been developed that leverage intrinsic hardware such as the camera, Bluetooth, USB, and audio port (A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," *Proc. Natl. Acad. Sci.*, vol. 111, no. 33, pp. 11984-11989, August 2014; P. B. Lillehoj, M.-C. Huang, N. Truong, and C.-M. Ho, "Rapid electrochemical detection on a mobile phone," *Lab. Chip*, vol. 13, no. 15, pp. 2950-2955, July 2013; B. Berg, B. Cortazar, D. Tseng, H. Ozkan, S. Feng, Q. Wei, R. Y.-L. Chan, J. Burbano, Q. Farooqui, M. Lewinski, D. Di Carlo, O. B. Garner, and A. Ozcan, "Cellphone-Based Hand-Held Microplate Reader for Point-of-Care Testing of Enzyme-Linked Immunosorbent Assays," *ACS Nano*, vol. 9, no. 8, pp. 7857-7866, August 2015; V. Oncescu, D. O'Dell, and D. Erickson, "Smartphone based health accessory for colorimetric detection of biomarkers in sweat and saliva," *Lab. Chip*, vol. 13, no. 16, pp. 3232-3238, July 2013; X. Wang, M. R. Gartia, J. Jiang, T.-W. Chang, J. Qian, Y. Liu, X. Liu, and G. L. Liu, "Audio jack based miniaturized mobile phone electrochemical sensing platform," *Sens. Actuators B Chem.*, vol. 209, pp. 677-685, March 2015; C. Ionescu, P. Svasta, C. Tamas, C. Bala, and L. Rotariu, "Portable measuring and display unit for electrochemical sensors," in *Design and Technology in Electronic Packaging (SIITME), 2010 IEEE 16th International Symposium for,* 2010, pp. 215-218; S. K. J. Ludwig, C. Tokarski, S. N. Lang, L. A. van Ginkel, H. Zhu, A. Ozcan, and M. W. F. Nielen, "Calling Biomarkers in Milk Using a Protein Microarray on Your Smartphone," *PLoS ONE*, vol. 10, no. 8, p. e0134360, August 2015; S. K. J. Ludwig, H. Zhu, S. Phillips, A. Shiledar, S. Feng, D. Tseng, L. A. van Ginkel, M. W. F. Nielen, and A. Ozcan, "Cellphone-based detection platform for rbST biomarker analysis in milk extracts using a microsphere fluorescence immunoassay," *Anal. Bioanal. Chem.*, vol. 406, no. 27, pp. 6857-6866, June 2014; C. M. McGeough and S. O'Driscoll, "Camera Phone-Based Quantitative Analysis of C-Reactive Protein ELISA," *IEEE Trans. Biomed. Circuits Syst.*, vol. 7, no. 5, pp. 655-659, October 2013; L. Cevenini, M. M. Calabretta, G. Tarantino, E. Michelini, and A. Roda, "Smartphone-interfaced 3D printed toxicity biosensor integrating bioluminescent 'sentinel cells,'" *Sens. Actuators B Chem.*; K. Su, Q. Zou, J. Zhou, L. Zou, H. Li, T. Wang, N. Hu, and P. Wang, "High-sensitive and high-efficient biochemical analysis method using a bionic electronic eye in combination with a smartphone-based colorimetric reader system," *Sens. Actuators B Chem.*, vol. 216, pp. 134-140, September 2015; W. Xu, S. Lu, Y. Chen, T. Zhao, Y. Jiang, Y. Wang, and X. Chen, "Simultaneous color sensing of 02 and pH using a smartphone," *Sens. Actuators B Chem.*, vol. 220, pp. 326-330, December 2015; M. Zangheri, L. Cevenini, L. Anfossi, C. Baggiani, P. Simoni, F. Di Nardo, and A. Roda, "A simple and compact smartphone accessory for quantitative chemiluminescence-based lateral flow immunoassay for salivary cortisol detection," *Biosens. Bioelectron.*, vol. 64, pp. 63-68, February 2015; D. Zhang, Y. Lu, Q. Zhang, L. Liu, S. Li, Y. Yao, J. Jiang, G. L. Liu, and Q. Liu, "Protein detecting with smartphone-controlled electrochemical impedance spectroscopy for point-of-care applications," *Sens. Actuators B Chem.*, vol. 222, pp. 994-1002, Jan. 2016; E. H. Doeven, G. J. Barbante, A. J. Harsant, P. S. Donnelly, T. U. Connell, C. F. Hogan, and P. S. Francis, "Mobile phone-based electrochemiluminescence sensing exploiting the TSB On-The-Go' protocol," *Sens. Actuators B Chem.*, vol. 216, pp. 608-613, September 2015; A. Sun, T. Wambach, A. G. Venkatesh, and D. A. Hall, "A low-cost smartphone-based electrochemical biosensor for point-of-care diagnostics," in 2014 *IEEE Biomedical Circuits and Systems Conference (BioCAS)*, 2014, pp. 312-315), these devices are still external to the phone making them more burdensome to manage and transport than a fully integrated solution, dissuading frequent use. By integrating biosensors directly into a smartphone, smartwatch or any platform and leveraging the scalability, cost-effectiveness, and accuracy of electrochemical biosensing, which led to the success of glucose meter, one can develop much more accessible and seamless mHealth applications that promote adherence to frequent or continuous testing. Furthermore, in addition to being a boon for those who live with chronic illnesses, biosensors integrated into everyday items also enable other individuals who are either at risk for disease, trying to improve health and fitness, or curious about their well-being to routinely monitor themselves.

Figure 8:
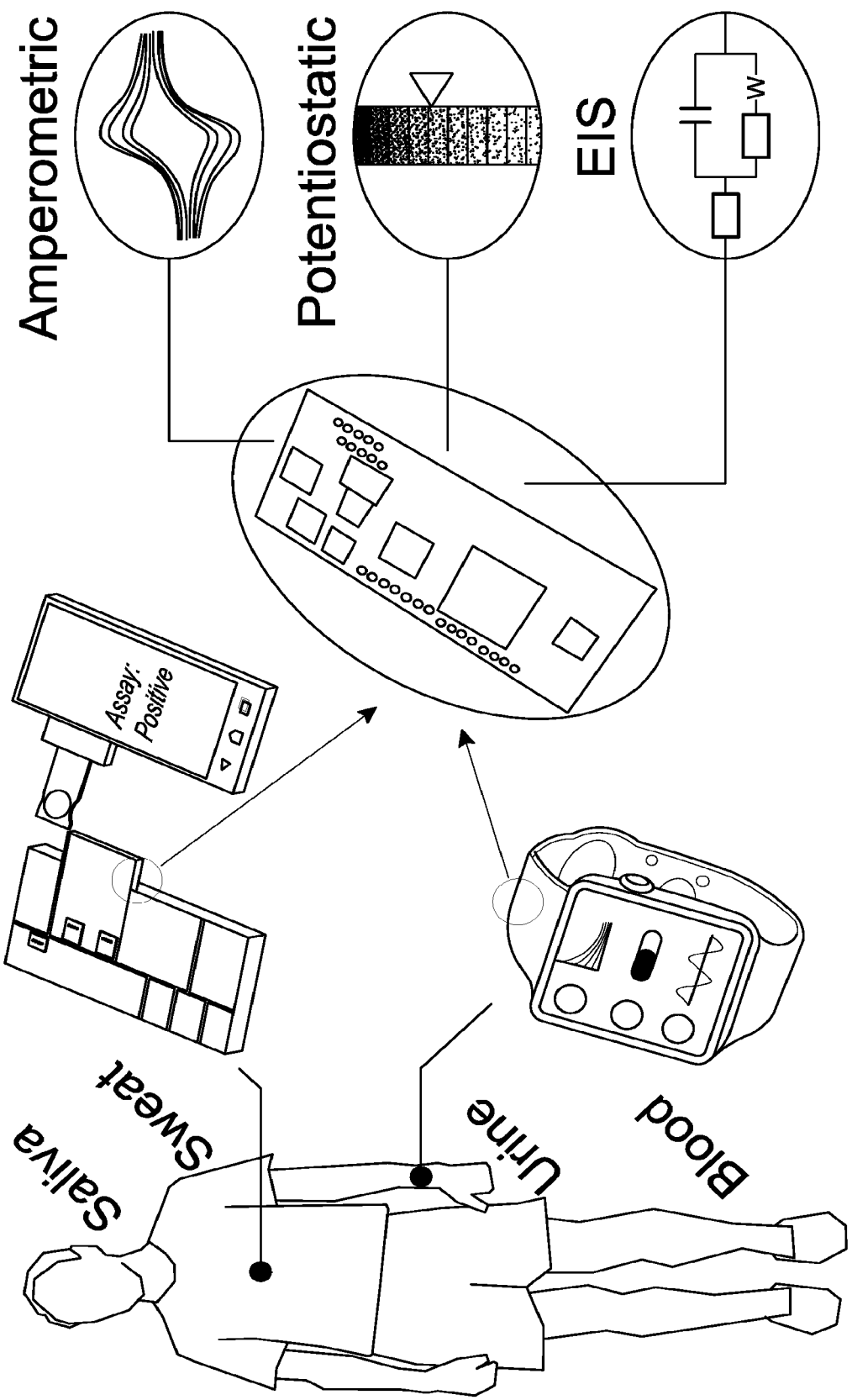
FIG. 8: Illustration showing potential uses for the multi-technique biosensor platform integrated into smartphones and wearable devices.

In some embodiments, the design of an electrochemical biosensor module for direct integration into a smartphone or wearable includes the use of a reconfigurable bipotentiostat capable of both supporting an extended range of techniques and, at the same time, conforming to the challenging size and power consumption constraints set by continually shrinking portable devices. While enabling a wide variety of tests would typically consume additional area and power, this design alleviates the problem by repurposing the same components in different measurement modes, ultimately reducing the redundancy. The entire platform (FIG. 8) can include the sensing module that houses the reconfigurable potentiostat that is meant to be built into a mobile device or wearable, an external sensor (disposable test strips, screen-printed electrodes, ion selective electrodes, etc.), and the mobile device or wearable itself. Since the external sensor component is in contact with the biological sample and is meant to be disposable, it is not permanently integrated into the smartphone, wearable, or platform like the rest of the module. However, when compared to non-integrated biosensors, which have this same external sensor constraint, smartphone or wearable integration ultimately eliminates having to carry around an extra hardware component thereby increasing accessibility. The mobile platform used can be Google's Project Ara modular smartphone, which allows the user to swap out different components and customize the phone's hardware. This platform can be used for biosensor integration because of its open and high-speed interface as well as its modularity that enables the smartphone to have biosensing, amongst many other, capabilities. However, the platform is not limited thereto and the platform can be any device or material, such as textile, that can integrate the reconfigurable potentiostat.

Electrochemical Sensing Background

As with other known POC electrochemical biosensors, the most crucial component is the potentiostat, or the analog front-end, that interfaces with and controls the electrodes in contact with the sample. A typical electrochemical cell includes a working electrode (WE), where the biochemical reaction occurs, and a reference electrode (RE), usually working in tandem with a counter electrode (CE) to set the potential of the cell. While there are numerous types of techniques which the potentiostat can conduct, each with varying sets of parameters, requirements, and advantages, all these methods essentially measure different aspects of the same phenomenon: the movement and displacement of charge at the interface between an electrode and an electrolytic solution, also known as an electrochemical cell. Equivalent circuit models of this electrochemical cell can be used to better understand the sensing mechanisms of various electrochemical techniques, thereby guiding the design and implementation as well as setting the requirements of the circuits tailored for each distinct test type.

Figure 9:
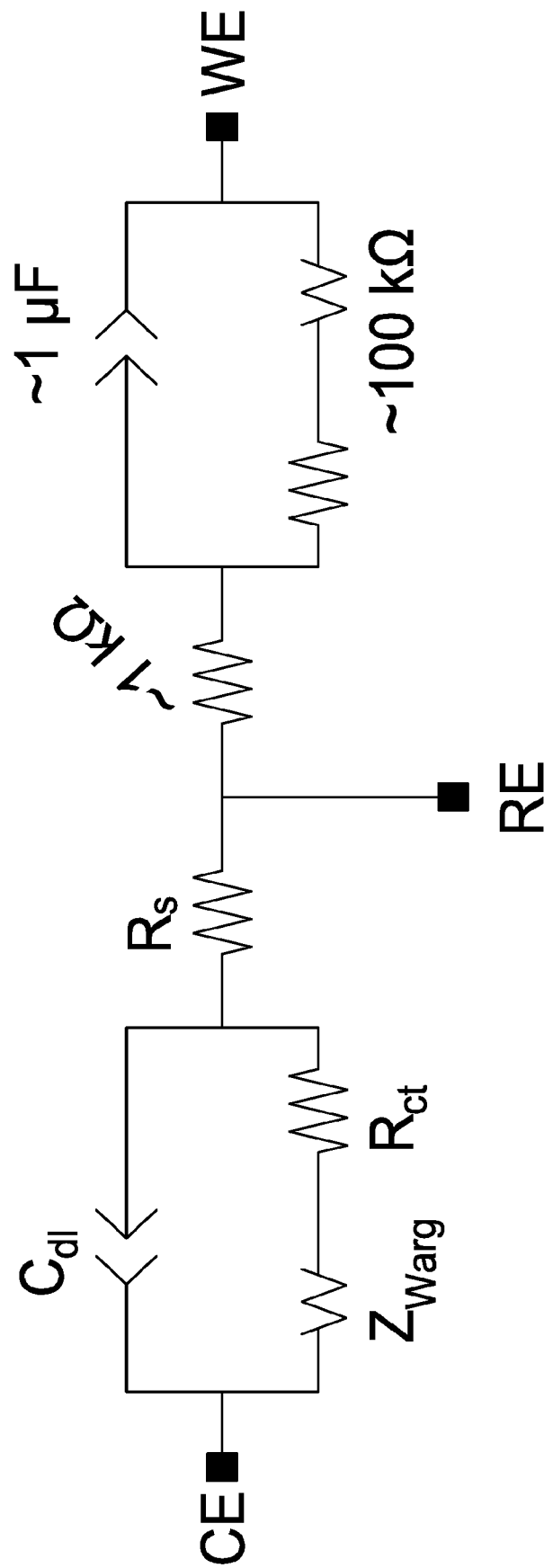
FIG. 9: Randles equivalent circuit model for a three electrode system.

Randles equivalent circuit (Allen J. Bard and Larry R. Faulkner, *Electrochemical Methods Fundamentals and Applications*, 2nd ed. Wiley, 2001), shown in FIG. 9 for a three electrode system, is the most widely used electrical model for characterizing the electrode-solution interface, and includes four main components: double-layer capacitance ($C_{dl}$), charge transfer resistance ($R_{ct}$), Warburg impedance ($Z_{warg}$), and solution resistance ($R_s$). $C_{dl}$ is a combination of the capacitance of the electrode itself and the capacitance generated by layers of ions and charged molecules forming at the surface of the electrode due to electrostatic forces. $C_{dl}$ is not a strict capacitance, and is typically modelled as a constant phase element with an impedance of $$Z_{dl} = \frac{1}{(j\omega)^m C_{dl}},$$

where m is the phase parameter. Typically, $C_{dl}$ ranges from about 0.1 to about 1 µF/mm² and is highly dependent on the salt concentration in solution as well as the voltage of the electrode (Allen J. Bard and Larry R. Faulkner, *Electrochemical Methods Fundamentals and Applications*, 2nd ed. Wiley, 2001; H.-J. Butt, K. Graf, and M. Kappl, *Physics and Chemistry of Interfaces*, 2nd ed. Weinheim: Wiley-VCH, 2006). $R_{ct}$ captures the transfer of electrons between the solution and electrode from reduction and oxidation reactions of molecules close to the surface. This resistance is typically about 10 to about 100 kΩ or approximately infinite in cases without the presence of redox molecules (non-faradic measurements) and varies with the concentration and type of molecule as well as the materials and voltage bias of the electrode. $Z_{warg}$ models the diffusion of redox molecules to and from the surface. Similar to $C_{dl}$, it also is a constant phase element component, but always with a 45° phase shift. Finally, $R_s$ models the ions drifting in bulk solution and is set by the solution conductivity and applied voltage. Depending on the measurement technique, different components of this model become important to the design of the potentiostat.

Amperometry is the standard method to perform most sensitive labelled assays, which use enzymatic tags that transduce and amplify a detection event into a measurable electrochemical signal. The circuitry for amperometric techniques (M. H. Nazari, H. Mazhab-Jafari, L. Leng, A. Guenther, and R. Genov, "CMOS Neurotransmitter Microarray: 96-Channel Integrated Potentiostat With On-Die Microsensors," *IEEE Trans. Biomed. Circuits Syst.*, vol. 7, no. 3, pp. 338-348, June 2013; M. M. Ahmadi and G. A. Jullien, "Current-Mirror-Based Potentiostats for Three-Electrode Amperometric Electrochemical Sensors," *IEEE Trans. Circuits Syst. Regul. Pap.*, vol. 56, no. 7, pp. 1339-1348, July 2009; M. Stanacevic, K. Murari, A. Rege, G. Cauwenberghs, and N. V. Thakor, "VLSI Potentiostat Array With Oversampling Gain Modulation for Wide-Range Neurotransmitter Sensing," *IEEE Trans. Biomed. Circuits Syst.*, vol. 1, no. 1, pp. 63-72, March 2007) applies a voltage waveform between the WE and RE using the CE to reduce voltage error while measuring the corresponding generated current signal at the WE, which is proportional to the concentration of the biomarker. For example, cyclic voltammetry (CV) and linear sweep voltammetry (LSV) both use slow (about 10 to about 100 mV/s) ramps (<1 V sweep range) to stimulate the electrochemical cell, while step-techniques such as chronoamperometry (CA) and square wave voltammetry (SWV) instead use pulsed voltages (a single step for CA and 10-100 Hz for SWV). In the majority of amperometry, the objective is to measure the current due to a particular redox reaction rather than from the faster charging and discharging of $C_{dl}$, referred to as background current. Even in pulsed techniques, the sections of the current measurement that includes the signal occur after the output has settled. Hence, amperometry necessitates precise voltage control and high measurement sensitivity for slow large signal currents.

While ions cannot be easily measured with traditional labelled assays or DC current measurements, their inherent charge and size allows them to be detected via potentiometric tests. Ion-selective electrodes (ISEs) separate specific ions with a semi-permeable membrane between two electrodes, thereby creating a potential difference (about 0.1 to about 100 mV) proportional to the amount of that ion concentration in the solution. However, due to the nature of these sensors, their impedance is very high, roughly on the order of 100 MΩ, necessitating high resolution sampling of the electrode voltage with a high input impedance.

For label-free electrochemical assays, electrochemical impedance spectroscopy (EIS) is most often used since it measures changes in impedance on the surface of an electrode due to displacement of charge (AGO or impeding of redox reactions ($\Delta R_{ct}$). Although there are many different circuit topologies that can implement EIS (A. Manickam, A. Chevalier, M. McDermott, A. D. Ellington, and A. Hassibi, "A CMOS Electrochemical Impedance Spectroscopy (EIS) Biosensor Array," *IEEE Trans. Biomed. Circuits Syst.*, vol. 4, no. 6, pp. 379-390, December 2010; A. Carullo, F. Ferraris, M. Parvis, A. Vallan, E. Angelini, and P. Spinelli, "Low-cost electrochemical impedance spectroscopy system for corrosion monitoring of metallic antiquities and works of art," *IEEE Trans. Instrum. Meas.*, vol. 49, no. 2, pp. 371-375, April 2000; H. Jafari, L. Soleymani, and R. Genov, "16-Channel CMOS Impedance Spectroscopy DNA Analyzer With Dual-Slope Multiplying ADCs," *IEEE Trans. Biomed. Circuits Syst.*, vol. 6, no. 5, pp. 468-478, October 2012), generally they all apply small amplitude (<10 mV) voltage sinusoids of varying frequencies (about 0.1 Hz to about 100 kHz) between a two electrode cell and record the resulting current. For each frequency, the magnitude and phase change is calculated and used to find the complex impedance ultimately forming an impedance spectrum that can be fitted to the Randles circuit. Unlike in traditional amperometry where aligning the timing of the input and output waveforms is often not necessary, EIS circuitry must not only have high enough bandwidth to measure these small signal AC currents but also have the ability to accurately track phase change between the applied voltage and measured current. Furthermore, any frequency dependent phase shift introduced by the measurement circuitry must be calibrated out.

Design of Reconfigurable Module

Figure 10:
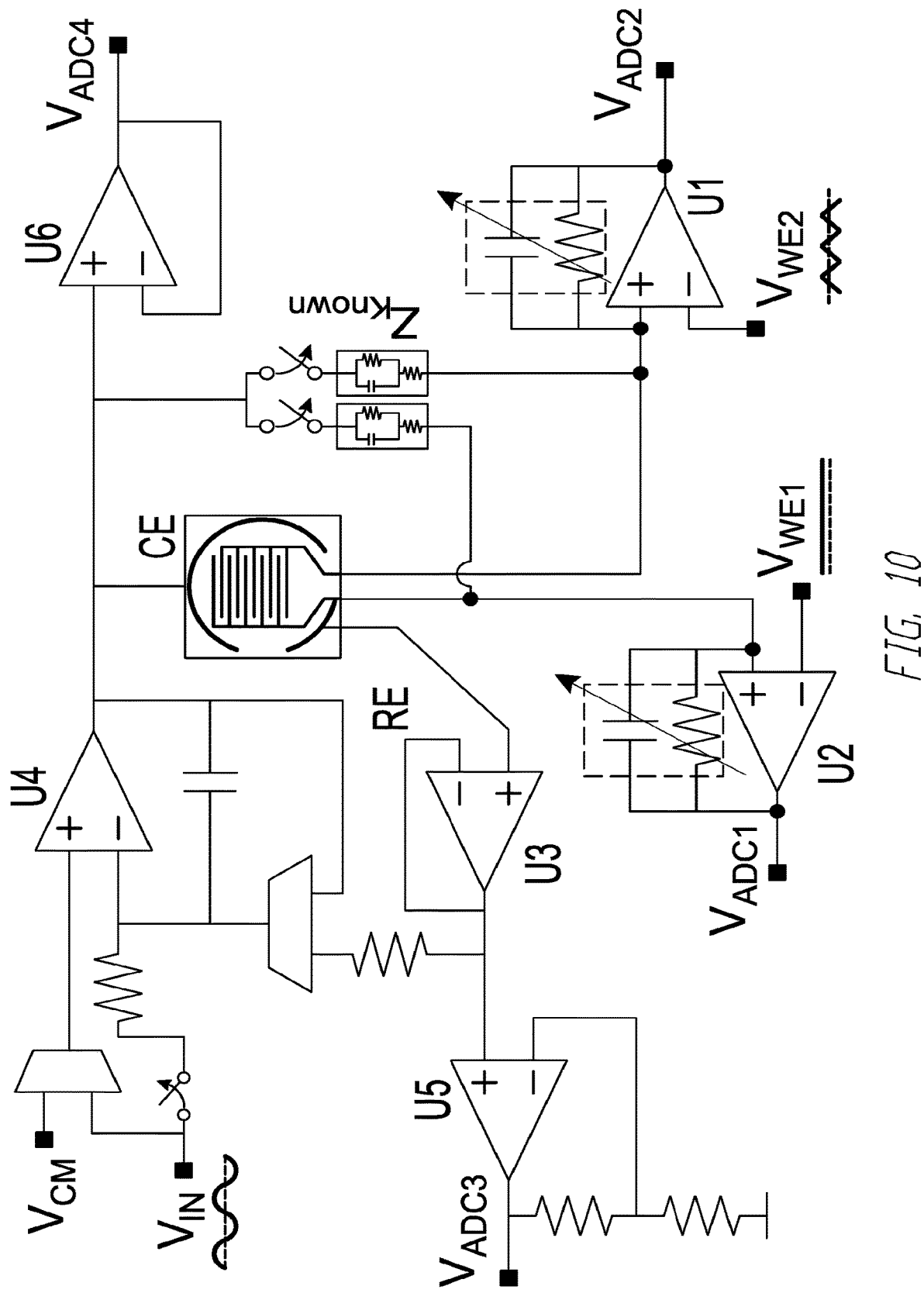
FIG. 10: Schematic of reconfigurable potentiostat where $V_{CM}$, $V_{IN}$, $V_{WE1}$, and $V_{WE2}$ are DAC outputs and $V_{ADC1-4}$ are ADC inputs.

In some embodiments, the potentiostat discussed is based on a well-studied and commonly used topology in electrochemistry (M. Vergani, M. Carminati, G. Ferrari, E. Landini, C. Caviglia, A. Heiskanen, C. Comminges, K. Zor, D. Sabourin, M. Dufva, M. Dimaki, R. Raiteri, U. Wollenberger, J. Emneus, and M. Sampietro, "Multichannel Bipotentiostat Integrated With a Microfluidic Platform for Electrochemical Real-Time Monitoring of Cell Cultures," *IEEE Trans. Biomed. Circuits Syst.*, vol. 6, no. 5, pp. 498-507, October 2012; L. Li, X. Liu, W. A. Qureshi, and A. J. Mason, "CMOS Amperometric Instrumentation and Packaging for Biosensor Array Applications," *IEEE Trans. Biomed. Circuits Syst.*, vol. 5, no. 5, pp. 439-448, October 2011), and is an expanded and improved version of our previous work (A. Sun, T. Wambach, A. G. Venkatesh, and D. A. Hall, "A multitechnique reconfigurable electrochemical biosensor for integration into mobile technologies," in 2015 *IEEE Biomedical Circuits and Systems Conference (BioCAS)*, 2015, pp. 1-4). However, to enable a large set of possible mHealth applications, the potentiostat must be able to run multiple types of techniques discussed above, which require different sensing modes and additional circuitry. Each of these various types of tests would typically require a different and separate set of circuitry. However, space and power are highly constrained resources on a mobile device and commodities must be shared with the device's other components. Therefore, in some embodiments, in order to reduce the area and, more importantly when moving to an integrated circuit implementation, the power, a single reconfigurable design (FIG. 10), rather than three different sets of potentiostat circuits, is used that repurposes components from one mode to the next while maintaining performance across different techniques. Hence, in some embodiments, the potentiostat is designed to support three distinct techniques: 1) amperometric, 2) potentiometric, and 3) impedance spectroscopy.

To further increase the flexibility and compatibility of the platform with POC type of tests, in some embodiments, the potentiostat includes dual WEs each with its own resistive feedback transimpedance amplifier (TIA), which is based on circuit topology commonly used in potentiostats (A. A. Rowe, A. J. Bonham, R. J. White, M. P. Zimmer, R. J. Yadgar, T. M. Hobza, J. W. Honea, I. Ben-Yaacov, and K. W. Plaxco, "CheapStat: An Open-Source, 'Do-It-Yourself' Potentiostat for Analytical and Educational Applications," *PLoS ONE*, vol. 6, no. 9, p. e23783, September 2011; S. Hwang and S. Sonkusale, "CMOS VLSI Potentiostat for Portable Environmental Sensing Applications," *IEEE Sens. J.*, vol. 10, no. 4, pp. 820-821, 2010; I. Ramfos, N. Vassiliadis, S. Blionas, K. Efstathiou, A. Fragoso, C. K. O'Sullivan, and A. Birbas, "A compact hybrid-multiplexed potentiostat for real-time electrochemical biosensing applications," *Biosens. Bioelectron.*, vol. 47, pp. 482-489, September 2013). Using networks of switches that can switch between a range of different resistors and capacitors, each TIA can have independently adjustable gain (for example, 10 kΩ, 100 kΩ, and 1 MΩ) and bandwidth (for example, 1 Hz-100 kHz), expanding its dynamic range and allowing it to measure different types of biomarkers that have varying sensitivity requirements. Although certain values are mentioned for the adjustable gain and bandwidth, the values are not limited thereto and a variety of values can be used to fit the desired type of test being performed.

This dual WE functionality also enables two tests of the same technique to be run simultaneously on the same sample, allowing one to either be a control to compensate for factors such as temperature variation or background signals, or an additional sensor for another biomarker. In some embodiments, in order to take advantage of this parallel testing, an assay must either generate no free-roaming redox molecules that can diffuse between electrodes and cause interference (e.g., label free assays) or use an electrode design that physically isolates or spreads out the sensing surfaces using wells or additional sample collection channels. Alternatively, the two electrodes can be used together for redox cycling with an interdigitated electrode in order to chemically amplify the signal for higher sensitivity, particularly when dealing with micro- and nano-scale sensors (J. Das, K. Jo, J. W. Lee, and H. Yang, "Electrochemical Immunosensor Using p-Aminophenol Redox Cycling by Hydrazine Combined with a Low Background Current," *Anal. Chem.*, vol. 79, no. 7, pp. 2790-2796, April 2007). The common-mode voltage is adjustable to accommodate and optimize the various current and voltage ranges, which can be skewed either to the positive or negative side depending on the expected response. The different configurations and respective performance are discussed in the following sections.

Amperometric

Figure 11:
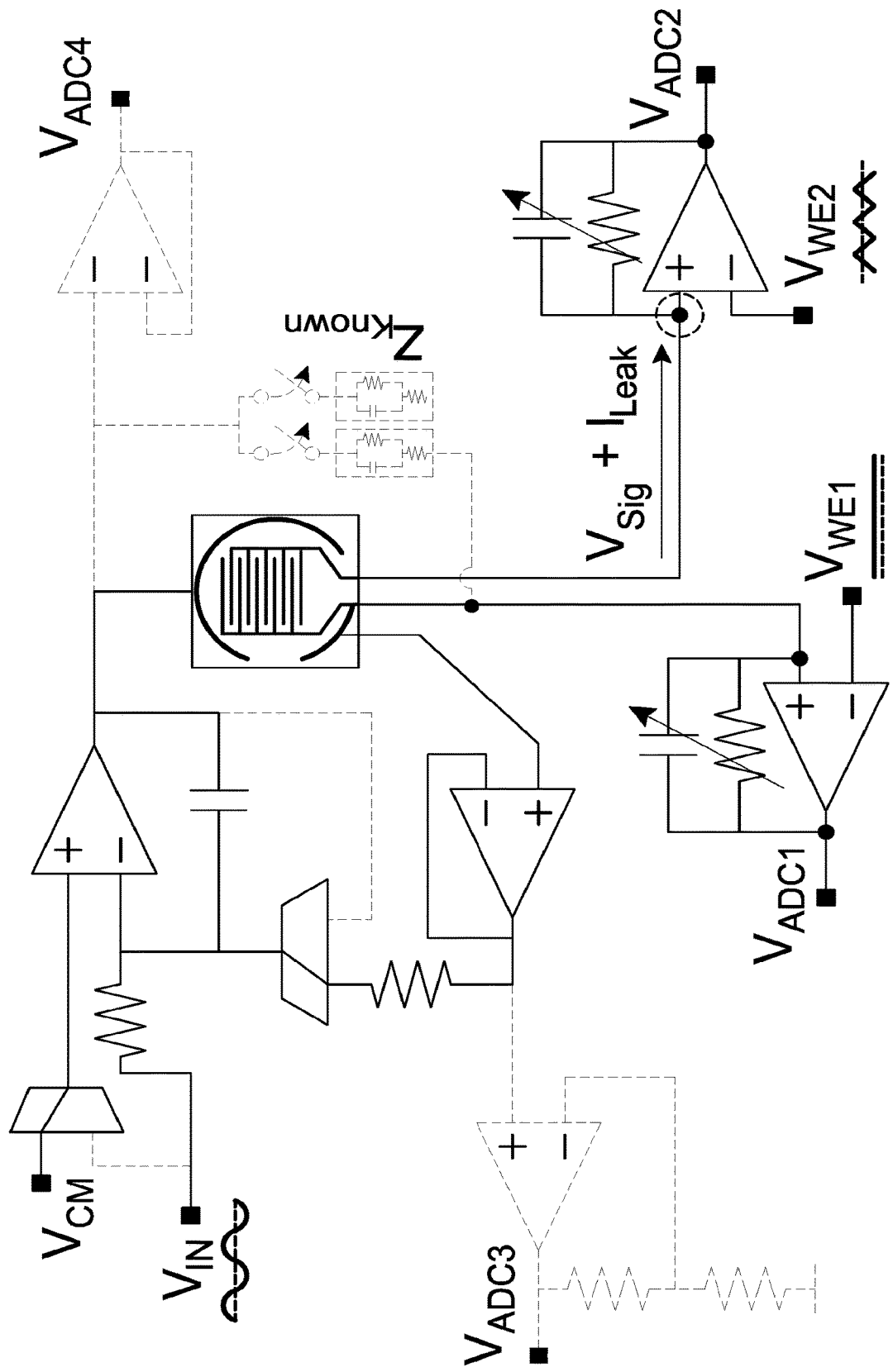
FIG. 11: Simplified schematic of the potentiostat in amperometric mode.

The potentiostat configuration for this mode is shown in FIG. 11. A voltage signal is applied to the three electrode sensor between the RE and the WE, with the CE supplying the current to set the solution potential. This voltage waveform, which varies depending on the technique chosen, generates a current signal in the solution that is measured at the WE, in this case, with a resistive feedback TIA. To expand the possible applications of the device, this potentiostat version can have two working electrodes with each channel having TIAs with independently configurable gain and bandwidth (adding one of, for example, 1, 10, and 100 nF capacitors in parallel with the feedback resistance). The variable gain allows the device to adjust for the different baseline currents and varying physiological concentration ranges of different biomarkers, assays, and sensor areas. Also, since different amperometric techniques excite the electrochemical cell with different input voltage waveforms, the bandwidth of the generated current signal can vary.

Since the sensitivity of these measurements depends on how accurately current can be measured, one of the most important design considerations for this mode are the input-referred noise of the TIA and the current leakage at the WE node. Hence, in some embodiments, all of the switches were chosen to have low leakage (less than about 20 pA) and the opamps (U1 and U2, for example, Analog Devices AD8552) were selected to balance the power, input bias current (160 pA), and noise. The requirements at the other electrodes are less constrained. In some embodiments, the input bias current of the RE circuitry must be minimized in order to reduce the IR error of the applied voltage. For example, by using a very low input bias opamp (U3, for example, Analog Devices AD8691) chosen specifically for the potentiometric mode (described later), this design can achieve an RE leakage of about 200 fA, which, with a typical solution resistance of about 100Ω, contributes about 100 nV error which is negligible. Furthermore, since the CE, which is controlled by U4 (for example, Texas Instruments OPA2333), only needs to be able to supply the necessary current to the cell for this mode, the parameters for the control circuitry are set by the EIS mode.

Potentiometric

Figure 12:
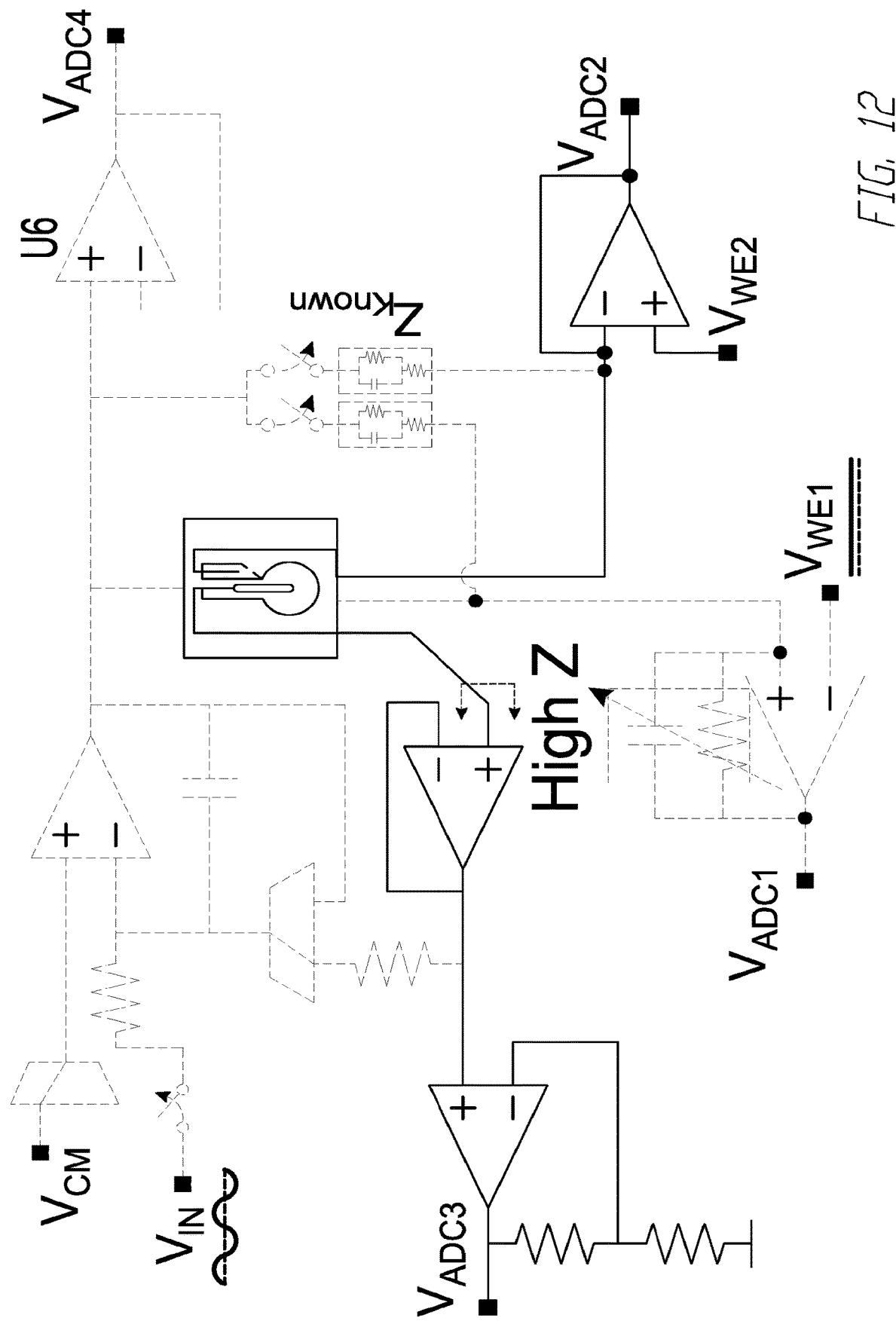
FIG. 12: Simplified schematic of the potentiostat in potentiometric mode.

In some embodiments, in the potentiometric mode (FIG. 12), the voltage generated between two electrodes in a solution is measured. Typically, an ISE requires measurement circuitry with an input bias current of less than about 1 pA to ensure that measurement error is less than about 1%. Without adding a new set of components, the input buffer used for RE in the amperometric mode is switched into the signal path for use as a high impedance input with a working electrode operating as the other terminal. By adjusting the bandwidth switches to provide a short, the WE circuitry in this case operates as a buffer and allows the voltage from sensor to either be sampled single-ended or pseudo-differentially to reject common-mode signals.

Impedance Spectroscopy

Figure 13:
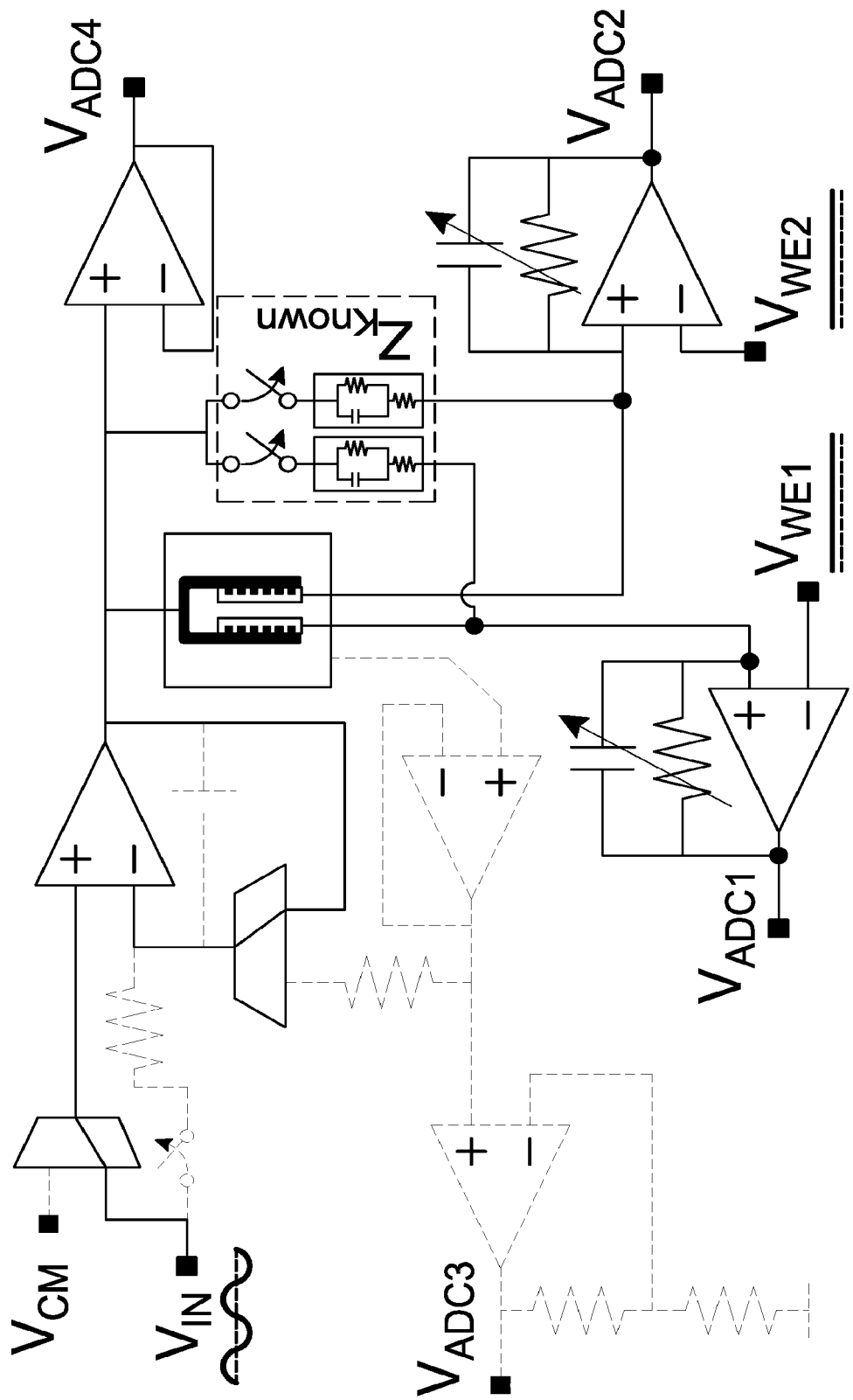
FIG. 13: Simplified schematic of the potentiostat in EIS mode.

In some embodiments, in the EIS mode (FIG. 13), a two-electrode sensor is attached between the CE and a single WE, with the option of attaching an additional sensor on the other WE. Small signal (about 20 mV) voltage sinusoids, with varying frequency from about 1 Hz to about 10 kHz, can be applied between the two terminals and the WE measures the resulting current. The gain and bandwidth of the WE TIA is adjusted depending on the impedance and frequency being measured, changing if the signal is too small or if the channel becomes saturated. In the two other modes, the open switches and unused electrodes can be low impedance nodes set to known voltages in order to avoid instability and interference. However, in some embodiments, in the EIS mode, the RE input is left floating in the circuitry in order to avoid the leakage current from adding a switch at this node, which is crucial for accurate amperometric and potentiometric measurements. However, the RE can be tied directly to the CE through a short on the electrode without affecting the impedance measurements as it can be incorporated into the calibration.

Making the approximation that the system is linear, due to the stimulus being small, the complex impedance $Z_{Cell}$ is computed as:

$$Z_{Cell}(j\omega) = H(j\omega)\frac{V_{IN}(j\omega)}{V_{OUT}(j\omega)} \quad (1)$$

where H(jω) is the transfer function that converts the current to voltage, $V_{IN}$ is the voltage sinusoid applied to the $Z_{Cell}$, and $V_{OUT}$ is the voltage read by the ADC. H(jω) in not only dependent on the feedback network of the TIA, which changes depending on the cell impedance, but also other factors such as parasitics in the switching networks and phase shift in the signal path. Hence, to account for varying H(jω) and compensate the channel accordingly, known test impedances ($Z_{Known}$) measured prior to use, one for each WE, can be switched in between the two electrodes, given the same stimulus, and measured at each frequency before the actual sensor is tested.

$$H(j\omega) = Z_{Known}(j\omega)\frac{V_{IN}(j\omega)}{V_{Measured}(j\omega)}, \quad (2)$$

$$Z_{Known}(j\omega) = R_s + \frac{1}{j\omega C}\|R_{ct}$$

Using known impedance measurements, the transfer function of the channel can be determined for each frequency (Eq. 2) and used to calibrate the impedance measurements in software on the host device (J. S. Daniels, E. P. Anderson, T. H. Lee, and N. Pourmand, "Simultaneous measurement of nonlinearity and electrochemical impedance for protein sensing using two-tone excitation," in 30*th Annual International Conference of the IEEE Engineering in Medicine and Biology Society,* 2008. *EMBS* 2008, 2008, pp. 5753-5756). Furthermore, to ensure that the input signal is correctly aligned with the output, the ADC can simultaneously measure the CE voltage, thereby reducing phase error introduced by the control circuitry.

Integration with Mobile Technology

Figure 14:
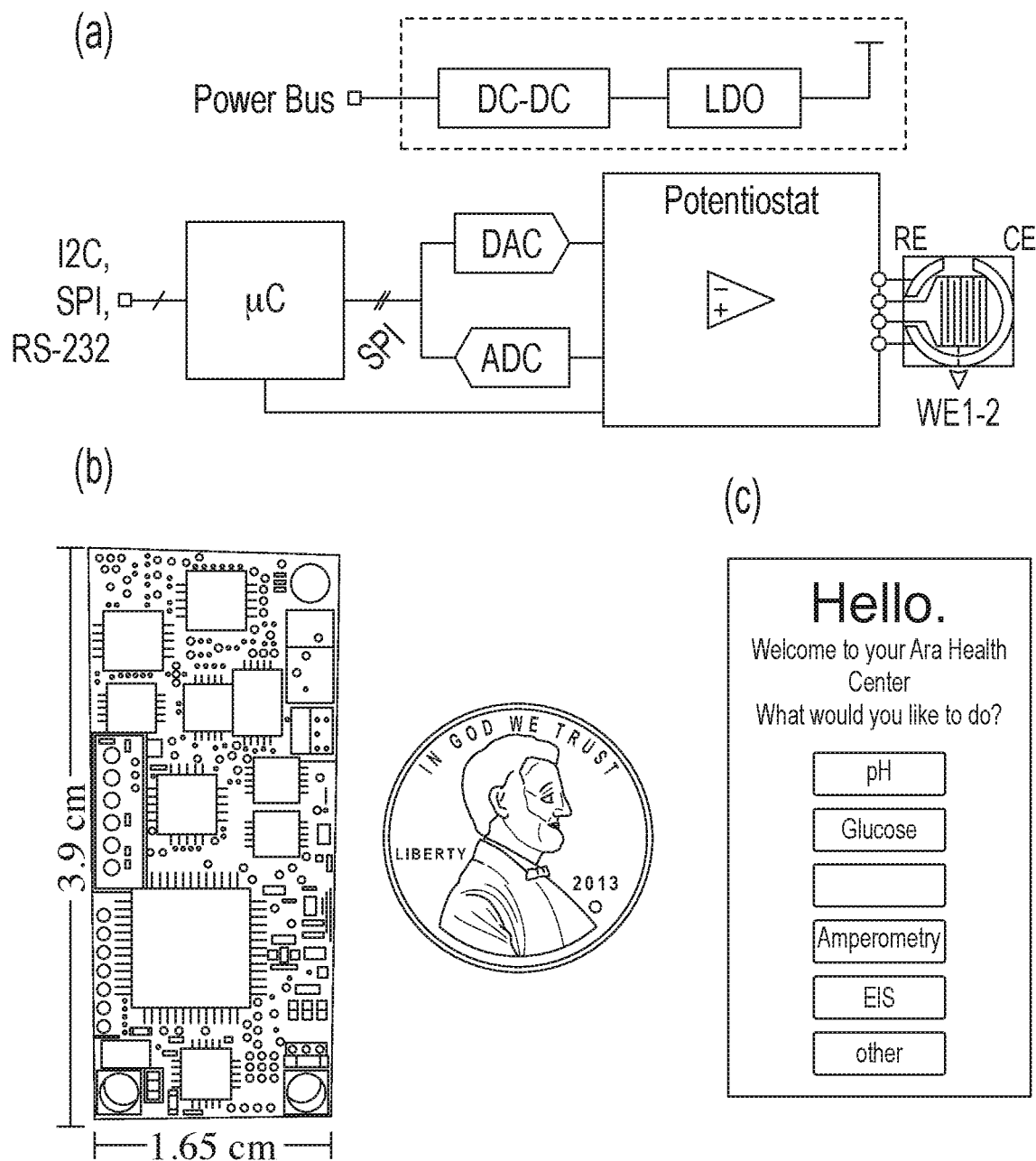
FIG. 14: a) Block diagram of the entire module b) Photograph of PCB next to a US penny for scale c) Screenshot of smartphone application interface.

As shown in FIG. 14(a), aside from the potentiostat, the module can also include a power regulation network, a DAC (for example, Analog Devices AD5685R), an ADC (for example, Analog Devices AD7682), and a microcontroller (for example, Microchip dsPIC33EP256MC204). This periphery circuitry can be easily tailored to the specifications of the wearable or mobile device. The design can take its power from the host device with an input voltage anywhere from about 2.5 to about 5.5 V and with a light-load efficient buck-boost DC-DC converter (for example, Texas Instruments LM366SD) in series with two LDOs (for example, Texas Instruments TPS79101) regulates it to both about 4 V and about 3.3 V, thereby isolating the analog and digital supplies. The DAC (14-bits) and ADC (16-bits) both have 4 channels, and, via SPI, their maximum update and sample rates are around 200 kHz. The microcontroller controls the potentiostat during testing by updating and sampling from the proper DAC and ADC channels respectively. The microcontroller also communicates with the host device via serial communication (either SPI, I²C, or RS-232 depending on the mobile device interface) and configures the potentiostat with the proper settings. In some embodiments, in order to integrate this module into a mobile device that is not a modular smartphone, an internal I/O port needs to be accessible. While this communication between the module and processor would usually be through a proprietary communication protocol, it can be reasonable to expect that for mobile devices that use different types of sensors (such as accelerometers and pulse oximeters) the translation hardware is already available that implements the required communication interface between sensors and the high-speed processor bus. Hence, adding this module would be as simple as integrating any other sensor.

In one experiment, a 3.9×1.65 cm² 4-layer PCB (FIG. 14(b) with discrete ICs was fabricated to fit into the Google Project Ara smartphone as a 2×1 sized module and work with an Android application shown in FIG. 14(c). Furthermore, this prototype was small enough to be compatible with wearable devices as well. The module communicates with the Spiral 1 Ara platform via the I²C serial communication pins of the microcontroller. For testing purposes, we used several off-the-shelf sensors with varied connectors. Hence, an interposer board to accommodate all the electrodes was also constructed and attached to the top or bottom of the module. Since the sensing areas are smaller than the module itself, actual developed and complete mobile devices can have the sensor or the sensor holder, in the case of disposable test strips, mounted directly into the shell of the device without altering the form factor.

Electrical Measurement Data

In the above experiment, each of the three modes were characterized and tested to verify their functionality. For the amperometric mode, since the sensitivity of these measurements depends on how accurately current can be measured, one of the most important design considerations for this mode are the input-referred noise, which was measured with 100 kΩ gain and a 1 kHz bandwidth to be 216 $pA_{RMS}$, and the leakage current at the input of the TIAs or WE. Since low leakage switches for selecting the gain and bandwidth are used and the number of connections to the inverting node is minimized, the overall input leakage (about 180 pA) is dominated by the input bias current of the opamp. Hence, we can measure bidirectional currents ranging from about 500 pA to 200 about μA, which is ideal for most POC applications. For the potentiometric mode, the input bias current of the measurement circuitry is about 200 fA, setting the approximate input impedance at 5 TΩ. The input referred voltage noise is 1.060 $μV_{RMS}$ (10 Hz bandwidth), and the voltage offset is about 400 μV. For EIS, when testing a known impedance of 100 kΩ in parallel with 1 μF from about 1 Hz to about 10 kHz, the module was measured to have a 5% magnitude and a 6° phase error as compared with a benchtop EIS tool. This configuration and calibration scheme described previously can measure an impedance range of 50Ω-10 MΩ.

Figure 15:
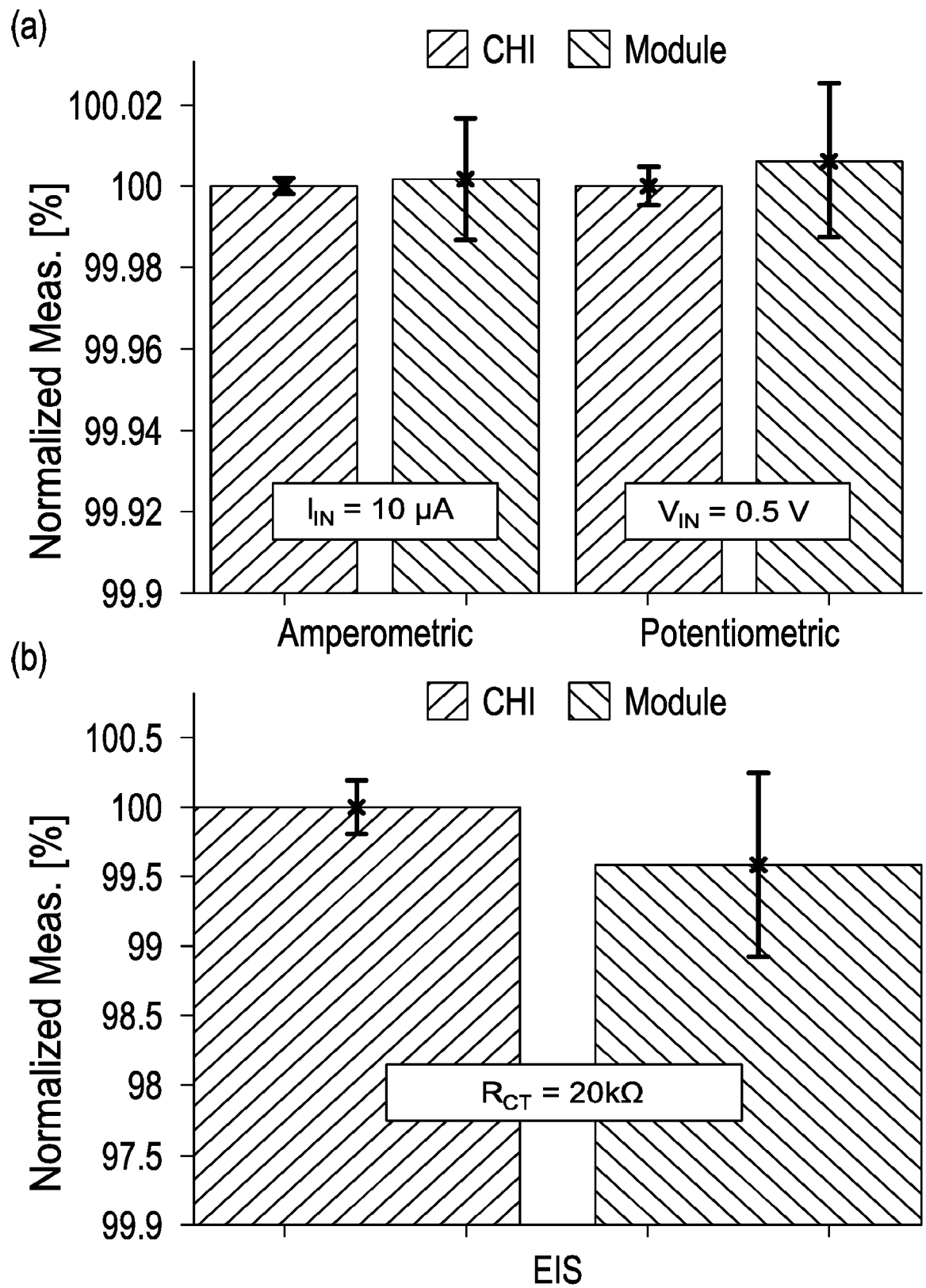
FIG. 15: a) Plots of the amperometric, potentiometric and b) EIS mode repeated measurements for both the CHI and module potentiostat for N=100 normalized to the CHI average.

To demonstrate the reproducibility and stability of all modes, a series of repeated measurements (N=100) on known inputs was performed using both the smartphone integrated platform and a benchtop potentiostat (CH Instruments 750E) also referred to in this paper as CHI. For the amperometric mode, a signal current of 10 μA was generated by applying a voltage signal across a model of an electrochemical cell made from circuit components resembling a simplified version of Randles equivalent circuit model ($R_{ct}$=200 kΩ, $C_{dl}$=2 μF, and $R_s$=1 kΩ). For the potentiometric mode, an input voltage of 0.5 V was applied directly from the sourcemeter across two electrodes. Finally, for EIS, the same circuit model was measured by both instruments to find the value of the charge transfer resistance. The results, shown in FIG. 15, show the mean and standard deviation of the measurements normalized to the CHI data. While the variance in the data from the module is larger than that of the benchtop potentiostat (1.41 nA vs. 88.6 pA, 93.7 μV vs. 16.3 μV, and 0.630Ω vs. 0.186Ω), each is still within acceptable bounds for that particular technique and matches well with the CHI measurements.

These modes can also consume varying amounts of power, due to the different ADC sampling and data transfer rates required by each mode. Also, since the module can disable the potentiostat, ADC, and DAC, as well as make the microcontroller sleep, essentially shutting itself off when not measuring (<100 μW), the average runtimes of each technique also determine the overall energy used by each mode. The entire potentiostat's peak power consumption including the switches and multiplexors is about 9.6 mW. In some embodiments, to conserve space, many of the parts used in the potentiostat include more than one device in a single package making it difficult to power gate individual unused components, so the power consumption of the potentiostat can remain approximately the same across the different modes. The digital and mixed signal circuitry including the microcontroller, ADC, and DAC consume a maximum of about 49.5 mW in amperometric mode with a runtime of about 10 to about 200 s and about 46.2 mW in potentiometric mode for tests that last about 10 s. In EIS mode, this power consumption is about 111 mW for an average of about 130 s. To put these numbers into context, the lithium ion battery found in most of today's smartphones has a capacity of approximately 1500 mAh. Average idle time is around 50 hours (@ 108 mW), while talk time is about 10 hours (@ 540 mW). Hence, at the very worst, this module would about match the power consumption of the phone while idling, and consume 80% less than a phone call. Therefore, making a couple of several minute-long measurements per day should not add noticeably to battery drain of the mobile device.

Testing POC Applications

While the device itself can perform many types of electrochemical tests, the biomarkers detected in the following assays can be chosen for their POC applications. All these biomarkers, which have been tested in experiments, while some taking more effort and materials than others, do not require lab equipment to pre-process the samples and have been shown to be possible to measure at the POC.

A. Amperometric Testing

1. Glucose.

For Glucose experiments, PBS was spiked with various concentrations of Dextrose from Marcon (4912-12) to create the test solutions. Commercial glucose test strips (True Test Blood Glucose Strips) based on Glucose dehydrogenase-PQQ (GDH) were applied with the various test solutions (27-450 mg/dL) and measured with chronoamperometry (0.5 V step for 10 seconds) with both a benchtop instrument (CHI 750E) and the biosensor module. Since commercial glucose strips are optimized for small droplets of blood (a few microliters), 1 μL of each of the test solutions were used in these measurements. The results (FIG. 14) show that the measured currents (taken after 10 seconds) for each concentration measured by both instruments follow the same trend. The calibration curve demonstrates that the assay is in the correct region to be able to diagnose or monitor diabetes (positive >200 mg/dL according to the American Diabetes Association).

2. Lactoferrin.

Lactoferrin (LTF) is a common biomarker for infection found in various concentrations in bodily fluid such as sweat (J.-H. Park, G.-T. Park, I. H. Cho, S.-M. Sim, J.-M. Yang, and D.-Y. Lee, "An antimicrobial protein, lactoferrin exists in the sweat: proteomic analysis of sweat," Exp. Dermatol., vol. 20, no. 4, pp. 369-371, 2011), saliva (F. Mizuhashi, K. Koide, S. Toya, M. Takahashi, R. Mizuhashi, and H. Shimomura, "Levels of the antimicrobial proteins lactoferrin and chromogranin in the saliva of individuals with oral dryness," J. Prosthet. Dent.), urine (S. Arao, S. Matsuura, M. Nonomura, K. Miki, K. Kabasawa, and H. Nakanishi, "Measurement of Urinary Lactoferrin as a Marker of Urinary Tract Infection," J. Clin. Microbiol., vol. 37, no. 3, pp. 553-557, March 1999), tears (A. Kijlstra, S. H. Jeurissen, and K. M. Koning, "Lactoferrin levels in normal human tears.," Br. J. Ophthalmol., vol. 67, no. 3, pp. 199-202, March 1983), and stool (M. Joishy, I. Davies, M. Ahmed, J. Wassel, K. Davies, A. Sayers, and H. Jenkins, "Fecal Calprotectin and Lactoferrin as Noninvasive Markers of Pediatric Inflammatory Bowel Disease," J. Pediatr. Gastroenterol. Nutr., vol. 48, no. 1, pp. 48-54, Jan. 2009). In this case, the detection of LTF in urine is used to diagnose urinary tract infection. Unlike the detection of glucose which is enzymatic, the detection method used here is a sandwich assay similar to ELISA.

Gold DropSens electrodes were functionalized for detection of LTF. Anti-human LTF (Abcam #ab10110) was mixed with Traut's reagent (Pierce 26101), dropped on the gold working electrodes, and incubated overnight at −4° C. 2% BSA (Thermo Scientific 37525) was applied for 1 hour at room temperature to block the surface. Afterwards, various concentrations of LTF (Abcam #a78526) in 20 μL droplets were added to each electrode before adding the secondary antibody (Abcam #ab25811) and then the NeutrAvidin conjugated alkaline phosphatase (Thermo Scientific #31002). Each binding step lasted an hour and included washing in between. Finally, before running cyclic voltammetry on each electrode, the substrate, p-AminoPhenyl Phosphate (Santa Cruz Biotechnology sc-281392) was added and allowed to react for 10 minutes. The sweep range and scan rate were −0.2 V to 0.3 V and 25 mV/s, respectively.

Figure 16:
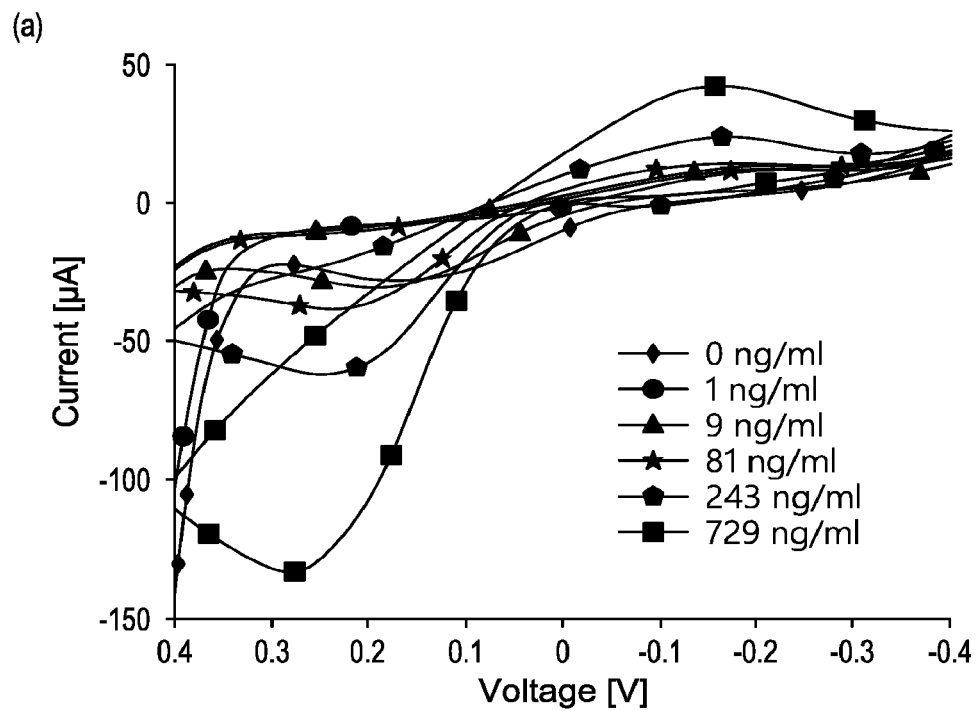
FIG. 16: a) CV curves for LTF measured by the sensing module and b) calibration curves for the LTF assay with the positive and negative diagnosis ranges annotated.
Figure 16:
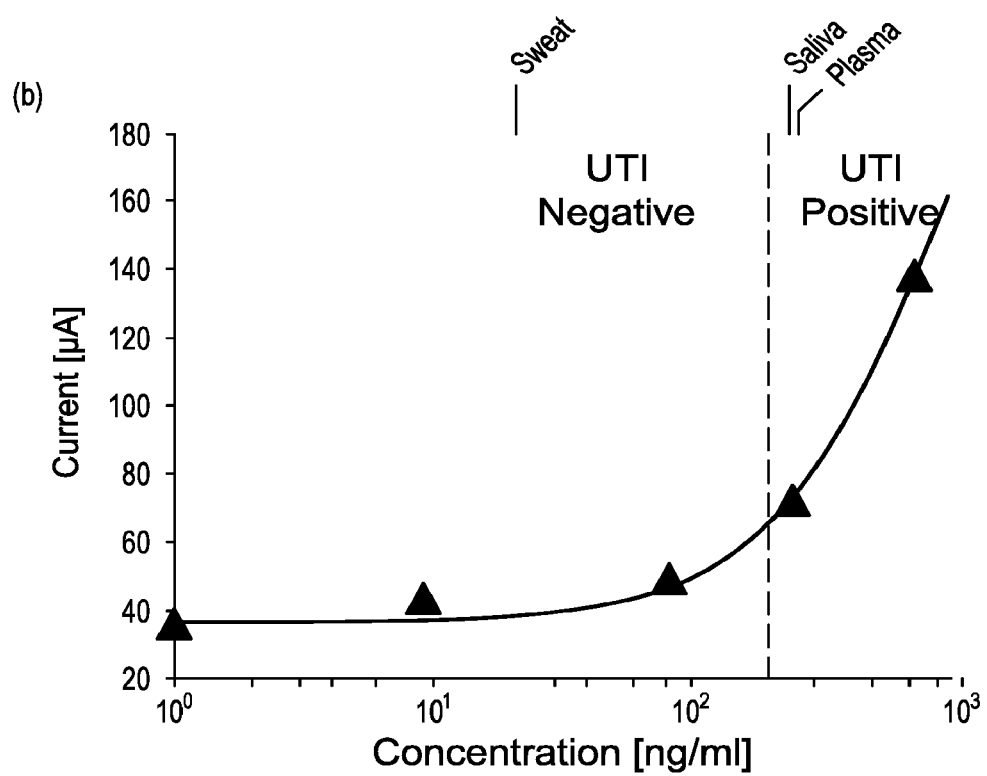

The concentration of LTF in the urine of a patient with and without an UTI is 3,300±646.3 ng/mL and 60.3±14.9 ng/mL, respectively (S. Arao, S. Matsuura, M. Nonomura, K. Miki, K. Kabasawa, and H. Nakanishi, "Measurement of Urinary Lactoferrin as a Marker of Urinary Tract Infection," *J. Clin. Microbiol.*, vol. 37, no. 3, pp. 553-557, March 1999). As shown in FIG. 16, the limit of detection of this assay is approximately ~1 ng/mL. Hence, LTF can be detected by this device in the diagnostically relevant range. Furthermore, the average LTF concentration in various bodily fluids in healthy patients is annotated on the same plot, demonstrating that this device could also be used to measure physiological LTF concentrations in these other fluids.

B. pH Measurements in Sweat pH levels in sweat secreted from the skin have been shown to correlate with hydration levels in the body (V. Oncescu, D. O'Dell, and D. Erickson, "Smartphone based health accessory for colorimetric detection of biomarkers in sweat and saliva," *Lab. Chip*, vol. 13, no. 16, pp. 3232-3238, July 2013). The higher the pH the more dehydrated someone is. Hence, by monitoring sweat during exercise, hydration can be tracked allowing the user to act accordingly to optimize his or her workout and avoid dangerous over exertion.

In order to first test the potentiostatic mode's accuracy when interfaced with a high impedance sensor, standard pH buffers from Thermo Scientific (910104, 910107, and 910110) were used as well as separately prepared phosphate buffers adjusted to specific values ranging from pH 4-10. All measurements were taken with an Oakton pH Probe (EW-35811-74). These buffers were measured with the biosensor module in potentiometric mode and verified with a table top pH meter (Orion Star A211). The maximum deviation was found to be 1.2% or 0.08 pH between the two measurement methods.

Figure 17:
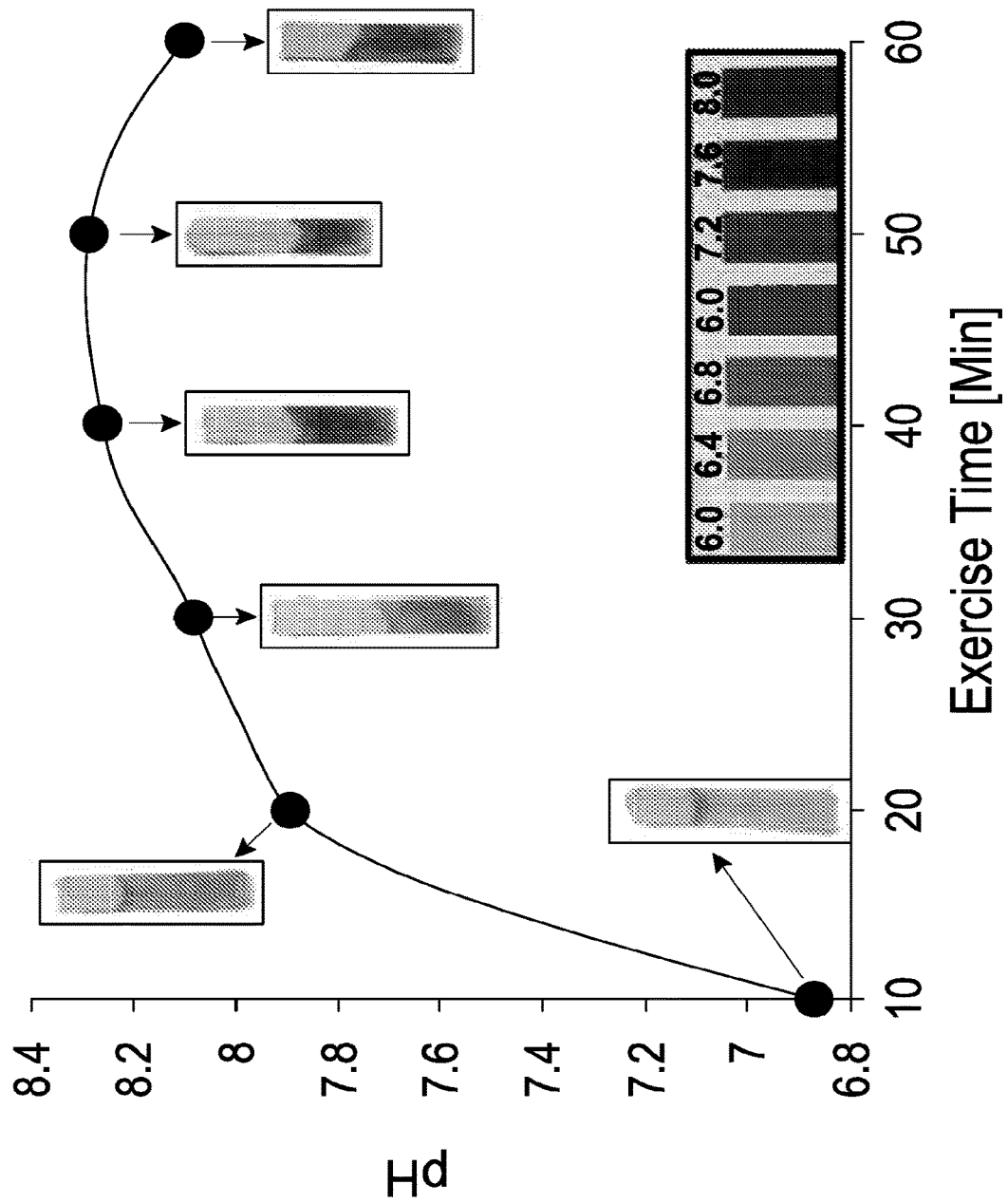
FIG. 17: Plot of pH levels of sweat from subject during exercise and the pH test strip result for each sample.

Next, 75 μL of sweat was collected at 10-minute intervals from a volunteer running at a steady pace for an hour. Afterwards, the sweat was tested with the module using a small pH electrode (VersaFlex VNIS/LD). Each sample was also tested using standard pH test strips (pHydrion Vivid 67). As shown in FIG. 17, the pH level increases steadily as more sweat is lost during the exercise as expected when compared to published data (V. Oncescu, D. O'Dell, and D. Erickson, "Smartphone based health accessory for colorimetric detection of biomarkers in sweat and saliva," Lab. Chip, vol. 13, no. 16, pp. 3232-3238, July 2013). The test strips line up with the pH levels measured by the device and serve to confirm this trend as well.

C. Label-Free Assay

The sensing of certain biomarkers, such as ions (H+, Na+, etc.) and some metabolites (glucose, lactose, etc.) especially those with large physiological concentrations, can be easily designed for portable POC use without an abundance of steps or reagents. However, assays for more complex molecules (peptides, proteins, DNA, etc.) that require much higher sensitivity to detect can be more cumbersome and time consuming for a user to conduct. For infrequent diagnostic tests, such as the labelled and highly sensitive UTI test discussed previously, the additional washing and reagent steps in the assay are manageable in the case of at-home testing. However, for more remote applications that require equally high sensitivity and increased portability, label-free techniques, such as EIS, are a promising solution as they do not use enzymatic labels to indirectly measure the biomarker, but rather physical and chemical changes, allowing for faster results with fewer assay steps (J. S. Daniels and N. Pourmand, "Label-Free Impedance Biosensors: Opportunities and Challenges," Electroanalysis, vol. 19, no. 12, pp. 1239-1257, 2007; E. Katz and I. Willner, "Probing Biomolecular Interactions at Conductive and Semiconductive Surfaces by Impedance Spectroscopy: Routes to Impedimetric Immunosensors, DNA-Sensors, and Enzyme Biosensors," Electroanalysis, vol. 15, no. 11, pp. 913-947, 2003). To demonstrate our module's label-free capabilities, we conducted an assay for the detection of NeutrAvidin using biotin immobilized on the surface of a gold electrode. NeutrAvidin is version of avidin, a protein that forms a specific and high-affinity bond with biotin, a pair commonly used as a preliminary model for label-free detection assays.

Figure 18:
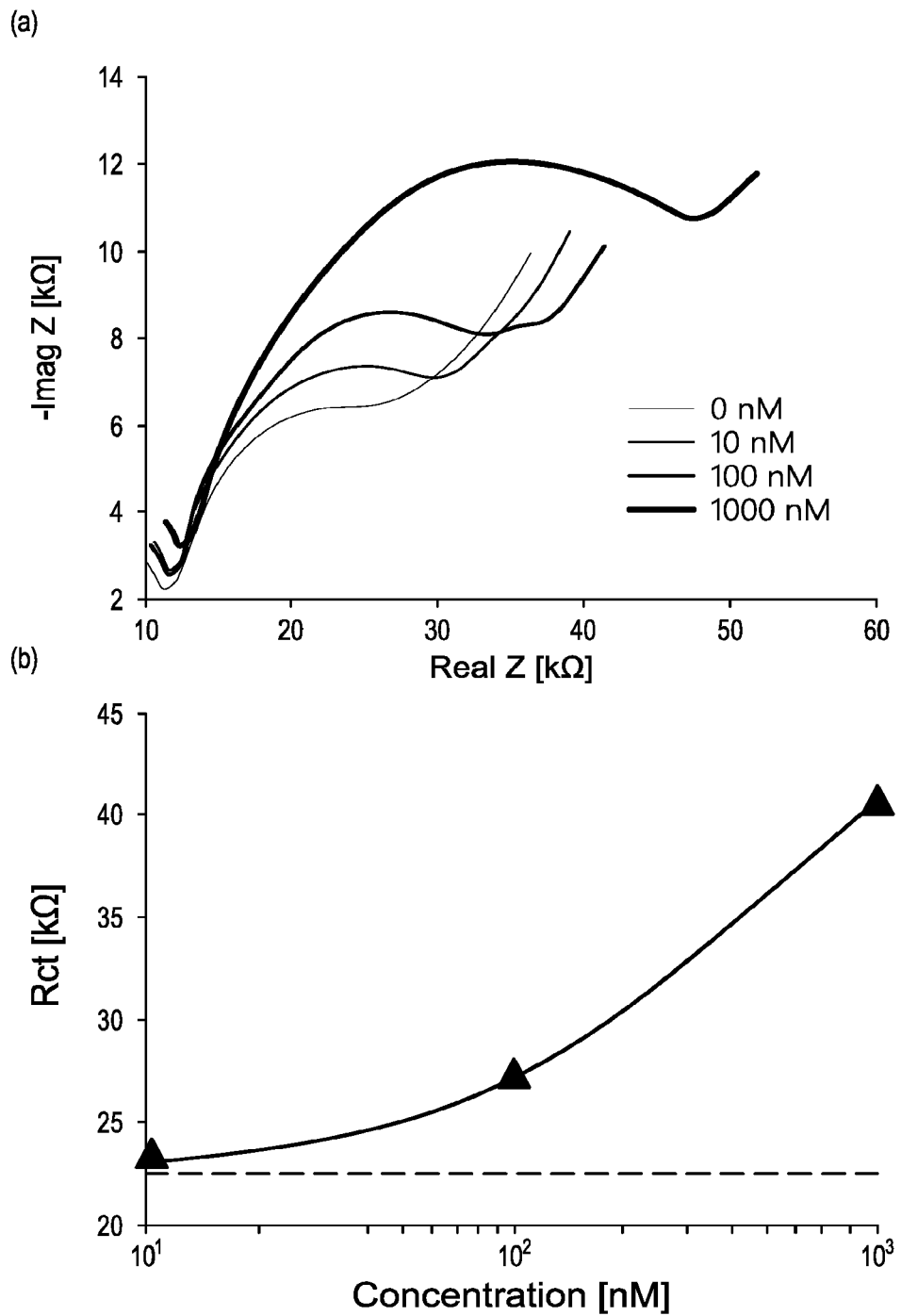
FIG. 18: a) Nyquist plot of each serial dilution of NeutraAvidin b) Concentration curve after fitting data Randles circuit to find charge transfer resistance with baseline drawn below.

Prior to the start of the assay, the electrode, 100 nm of gold sputtered onto a glass substrate, was cleaned with 1 mM KOH/$H_2O_2$ and functionalized with a 100 μM thiolated-biotin (Sigma-Aldrich #746622) reagent solution. After performing a washing and blocking, the electrode was ready for use. 20 μL droplets of different concentrations of NeutrAvidin (Thermo Scientific #31000) in a 1 mM ferro/ferricyanide ($K_4[Fe(CN)_6]$/$K_3[Fe(CN)_6]$) PBS buffer were added to the electrode, allowed to bind for 10 minutes, and then measured using EIS (1 Hz-10 kHz) with a Ag wire pseudo RE. These data were then fitted against the standard Randles circuit (Allen J. Bard and Larry R. Faulkner, *Electrochemical Methods Fundamentals and Applications*, 2nd ed. Wiley, 2001) to determine the change in charge transfer resistance, relevant in faradaic impedance measurements. The Nyquist plot of the results as well as the concentration curve, shown in FIG. 18, clearly demonstrate that this module can be used as a label-free biosensor. While NeutrAvidin itself is not a particularly useful biomarker, due to the mechanism of the biotin-avidin bonding, the results of this model assay demonstrate that this device can be generalized and used in most label-free affinity assays already developed (M. Xu, X. Luo, and J. J. Davis, "The label free picomolar detection of insulin in blood serum," Biosens. Bioelectron., vol. 39, no. 1, pp. 21-25, Jan. 2013; R. Ohno, H. Ohnuki, H. Wang, T. Yokoyama, H. Endo, D. Tsuya, and M. Izumi, "Electrochemical impedance spectroscopy biosensor with interdigitated electrode for detection of human immunoglobulin A," Biosens. Bioelectron., vol. 40, no. 1, pp. 422-426, February 2013; T. Bryan, X. Luo, P. R. Bueno, and J. J. Davis, "An optimised electrochemical biosensor for the label-free detection of C-reactive protein in blood," Biosens. Bioelectron., vol. 39, no. 1, pp. 94-98, Jan. 2013).

D. Comparison with Literature

These POC applications experiments demonstrate both the performance and the extensive functionality of the reconfigurable module. To closely examine the performance, Table 2 shows a comparison with state of the art portable biosensors that have been previously published. For each mode, our module approximately matches the performance of other platforms in terms of dynamic range, sensitivity, and error, while at the same time being able to reconfigure itself into these three different sensing modes. Hence, whereas other devices only have one or two of these measurement capabilities, this device is able to package all these multiple techniques with approximately equivalent performance into a single small form factor module.

TABLE 2

Comparison with State of the Art for All Electrochemical Modes

| | Amperometric | | Potentiometric | | EIS | | |
|---|---|---|---|---|---|---|---|
| Ref. | Dynamic Range | Sensitivity [nA] | pH Resolution | Input Z [Ω] | Frequency [Hz] | Z Range [Ω] | Mag./Phase Error |
| Rowe et al. 2011 | 54 dB (50 µA max) | 100 | — | — | — | — | — |
| Cruz et al. 2014 | 43.5 dB (750 µA max) | 5000 | — | — | — | — | — |
| Steinberg et al. 2015 | 51.1 dB (5.4 µA max) | 15 | — | — | — | — | — |
| Nemiroski et al. 2014 | 104 dB (78 µA max) | 0.5 | 8% | 5 TΩ | — | — | — |
| Oncescu et al. 2013 | — | — | 0.2 pH | N/A | — | — | — |
| Angelini et al. 2014 | — | — | — | — | 0.01-100k | 1k-1T | 5%, 3° |
| Punter-Villagrasa et al. 2014 | — | — | — | — | 10-100k | N/A | 12.3%, 12° |
| Zhang et al. 2016 | — | — | — | — | 10-10k | 1k-10M | N/A, 0.8° |
| Sun et al. 2016 | 106 dB (200 µA max) | <1 nA | 1.2%, 0.08 pH | ~5 TΩ | 1-10k | 50-10M | 5%, 6° |

CONCLUSION

We have built and demonstrated a reconfigurable, multi-technique biosensor platform specially designed for integration directly into mobile devices for diagnosing and monitoring the health of a user at the POC. By reusing components in different measurement modes, we can minimize the size and power of the design while at the same time keeping performance and expanding the functionality of the module for use in most POC applications. By adding this dedicated hardware directly into every day carry electronics, we hope to promote the use of specialized, portable, and practical medical devices well positioned to be the first line of defense in the future of healthcare.

Although certain experiment conditions and specifications are described, the various and devices, systems and methods described herein can be used under a variety of conditions and environments.

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm processes described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices such as general purposes computers, wireless communication device handsets, or integrated circuit devices having multiple uses including applications in wireless communication device handsets, automotive, appliances, wearables, and/or other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software or hardware configured for encoding and decoding, or incorporated in a combined video encoder-decoder (CODEC). Also, the techniques could be fully implemented in one or more circuits or logic elements.

The techniques of this disclosure may be implemented in a wide variety of devices or apparatuses, including a wireless handset, an integrated circuit (IC) or a set of ICs (for example, a chip set). Various components, or units are described in this disclosure to emphasize functional aspects of devices configured to perform the disclosed techniques, but do not necessarily require realization by different hardware units. Rather, as described above, various units may be combined in a codec hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

All references listed herein are incorporated herein by reference in their entireties, including the following references:

REFERENCES

U.S. Pat. No. 8,923,918 B2
U.S. Pat. No. 8,947,656 B2
US 2013/0012796 A1
US 2014/0012511 A1
US 2014/0099237 A1
US 2014/0170761 A1

M. M. Ahmadi and G. A. Jullien, "Current-Mirror-Based Potentiostats for Three-Electrode Amperometric Electrochemical Sensors," *IEEE Trans. Circuits Syst. Regul. Pap.*, vol. 56, no. 7, pp. 1339-1348, July 2009.

E. Angelini, S. Corbellini, M. Parvis, F. Ferraris, and S. Grassini, "An Arduino-based EIS with a logarithmic amplifier for corrosion monitoring," in Instrumentation and Measurement Technology Conference (I2MTC) Proceedings, 2014 IEEE International, 2014, pp. 905-910.

S. Arao, S. Matsuura, M. Nonomura, K. Mild, K. Kabasawa, and H. Nakanishi, "Measurement of Urinary Lactoferrin as a Marker of Urinary Tract Infection," *J. Clin. Microbiol.*, vol. 37, no. 3, pp. 553-557, March 1999.

Allen J. Bard and Larry R. Faulkner, *Electrochemical Methods Fundamentals and Applications*, 2nd ed. Wiley, 2001.

B. Berg, B. Cortazar, D. Tseng, H. Ozkan, S. Feng, Q. Wei, R. Y.-L. Chan, J. Burbano, Q. Farooqui, M. Lewinski, D. Di Carlo, O. B. Garner, and A. Ozcan, "Cellphone-Based Hand-Held Microplate Reader for Point-of-Care Testing of Enzyme-Linked Immunosorbent Assays," *ACS Nano*, vol. 9, no. 8, pp. 7857-7866, August 2015.

J. R. Blanco, F. J. Ferrero, J. C. Campo, J. C. Anton, J. M. Pingarron, A. J. Reviejo, and J. Manso, "Design of a Low-Cost Portable Potentiostat for Amperometric Biosensors," in *Proceedings of the IEEE Instrumentation and Measurement Technology Conference, 2006. IMTC 2006*, 2006, pp. 690-694.

T. Bryan, X. Luo, P. R. Bueno, and J. J. Davis, "An optimised electrochemical biosensor for the label-free detection of C-reactive protein in blood," Biosens. Bioelectron., vol. 39, no. 1, pp. 94-98, Jan. 2013.

H.-J. Butt, K. Graf, and M. Kappl, *Physics and Chemistry of Interfaces*, 2nd ed. Weinheim: Wiley-VCH, 2006.

A. Carullo, F. Ferraris, M. Parvis, A. Vallan, E. Angelini, and P. Spinelli, "Low-cost electrochemical impedance spectroscopy system for corrosion monitoring of metallic antiquities and works of art," *IEEE Trans. Instrum. Meas.*, vol. 49, no. 2, pp. 371-375, April 2000.

L. Cevenini, M. M. Calabretta, G. Tarantino, E. Michelini, and A. Roda, "Smartphone-interfaced 3D printed toxicity biosensor integrating bioluminescent 'sentinel cells,'" *Sens. Actuators B Chem.*

A. F. D. Cruz, N. Norena, A. Kaushik, and S. Bhansali, "A low-cost miniaturized potentiostat for point-of-care diagnosis," *Biosensors and Bioelectronics*, vol. 62, pp. 249-254, December 2014.

J. S. Daniels and N. Pourmand, "Label-Free Impedance Biosensors: Opportunities and Challenges," Electroanalysis, vol. 19, no. 12, pp. 1239-1257, 2007.

J. S. Daniels, E. P. Anderson, T. H. Lee, and N. Pourmand, "Simultaneous measurement of nonlinearity and electrochemical impedance for protein sensing using two-tone excitation," in 30*th Annual International Conference of the IEEE Engineering in Medicine and Biology Society*, 2008. EMBS 2008, 2008, pp. 5753-5756.

J. Das, K. Jo, J. W. Lee, and H. Yang, "Electrochemical Immunosensor Using p-Aminophenol Redox Cycling by Hydrazine Combined with a Low Background Current," *Anal. Chem.*, vol. 79, no. 7, pp. 2790-2796, April 2007.

E. H. Doeven, G. J. Barbante, A. J. Harsant, P. S. Donnelly, T. U. Connell, C. F. Hogan, and P. S. Francis, "Mobile phone-based electrochemiluminescence sensing exploiting the 'USB On-The-Go' protocol," *Sens. Actuators B Chem.*, vol. 216, pp. 608-613, September 2015.

C.-Y. Huang, M.-H. Lee, Z.-H. Wu, H.-Y. Tseng, Y.-C. Huang, B.-D. Liu, and H.-Y. Lin, "A Portable Potentiostat with Molecularly Imprinted Polymeric Electrode for Dopamine Sensing," in *IEEE Circuits and Systems International Conference on Testing and Diagnosis, 2009. ICTD 2009*, 2009, pp. 1-4.

S. Hwang and S. Sonkusale, "CMOS VLSI Potentiostat for Portable Environmental Sensing Applications," *IEEE Sens. J.*, vol. 10, no. 4, pp. 820-821, 2010.

C. Ionescu, P. Svasta, C. Tamas, C. Bala, and L. Rotariu, "Portable measuring and display unit for electrochemical sensors," in *Design and Technology in Electronic Packaging (SIITME), 2010 IEEE 16th International Symposium for*, 2010, pp. 215-218.

H. Jafari, L. Soleymani, and R. Genov, "16-Channel CMOS Impedance Spectroscopy DNA Analyzer With Dual-Slope Multiplying ADCs," *IEEE Trans. Biomed. Circuits Syst.*, vol. 6, no. 5, pp. 468-478, October 2012.

M. Joishy, I. Davies, M. Ahmed, J. Wassel, K. Davies, A. Sayers, and H. Jenkins, "Fecal Calprotectin and Lactoferrin as Noninvasive Markers of Pediatric Inflammatory Bowel Disease," *J. Pediatr. Gastroenterol. Nutr.*, vol. 48, no. 1, pp. 48-54, Jan. 2009.

E. Katz and I. Willner, "Probing Biomolecular Interactions at Conductive and Semiconductive Surfaces by Impedance Spectroscopy: Routes to Impedimetric Immunosensors, DNA-Sensors, and Enzyme Biosensors," *Electroanalysis*, vol. 15, no. 11, pp. 913-947, 2003.

A. Kijlstra, S. H. Jeurissen, and K. M. Koning, "Lactoferrin levels in normal human tears.," *Br. J. Ophthalmol.*, vol. 67, no. 3, pp. 199-202, March 1983.

L. Li, X. Liu, W. A. Qureshi, and A. J. Mason, "CMOS Amperometric Instrumentation and Packaging for Biosensor Array Applications," *IEEE Trans. Biomed. Circuits Syst.*, vol. 5, no. 5, pp. 439-448, October 2011.

P. B. Lillehoj, M.-C. Huang, N. Truong, and C.-M. Ho, "Rapid electrochemical detection on a mobile phone," Lab. Chip, vol. 13, no. 15, pp. 2950-2955, July 2013.

S. K. J. Ludwig, H. Zhu, S. Phillips, A. Shiledar, S. Feng, D. Tseng, L. A. van Ginkel, M. W. F. Nielen, and A. Ozcan, "Cellphone-based detection platform for rbST biomarker analysis in milk extracts using a microsphere fluorescence immunoassay," *Anal. Bioanal. Chem.*, vol. 406, no. 27, pp. 6857-6866, June 2014.

S. K. J. Ludwig, C. Tokarski, S. N. Lang, L. A. van Ginkel, H. Zhu, A. Ozcan, and M. W. F. Nielen, "Calling Biomarkers in Milk Using a Protein Microarray on Your Smartphone," *PLoS ONE*, vol. 10, no. 8, p. e0134360, August 2015.

A. Manickam, A. Chevalier, M. McDermott, A. D. Ellington, and A. Hassibi, "A CMOS Electrochemical Impedance Spectroscopy (EIS) Biosensor Array," *IEEE Trans. Biomed. Circuits Syst.*, vol. 4, no. 6, pp. 379-390, December 2010.

C. M. McGeough and S. O'Driscoll, "Camera Phone-Based Quantitative Analysis of C-Reactive Protein ELISA," *IEEE Trans. Biomed. Circuits Syst.*, vol. 7, no. 5, pp. 655-659, October 2013.

F. Mizuhashi, K. Koide, S. Toya, M. Takahashi, R. Mizuhashi, and H. Shimomura, "Levels of the antimicrobial proteins lactoferrin and chromogranin in the saliva of individuals with oral dryness," *J. Prosthet. Dent.*

M. H. Nazari, H. Mazhab-Jafari, L. Leng, A. Guenther, and R. Genov, "CMOS Neurotransmitter Microarray: 96-Channel Integrated Potentiostat With On-Die Microsensors," *IEEE Trans. Biomed. Circuits Syst.*, vol. 7, no. 3, pp. 338-348, June 2013.

A. Nemiroski, D. C. Christodouleas, J. W. Hennek, A. A. Kumar, E. J. Maxwell, M. T. Fernández-Abedul, and G. M. Whitesides, "Universal mobile electrochemical detector designed for use in resource-limited applications," *Proc. Natl. Acad. Sci.*, vol. 111, no. 33, pp. 11984-11989, August 2014.

R. Ohno, H. Ohnuki, H. Wang, T. Yokoyama, H. Endo, D. Tsuya, and M. Izumi, "Electrochemical impedance spectroscopy biosensor with interdigitated electrode for detection of human immunoglobulin A," *Biosens. Bioelectron.*, vol. 40, no. 1, pp. 422-426, February 2013.

V. Oncescu, D. O'Dell, and D. Erickson, "Smartphone based health accessory for colorimetric detection of biomarkers in sweat and saliva," *Lab. Chip*, vol. 13, no. 16, pp. 3232-3238, July 2013.

V. Oncescu, M. Mancuso, and D. Erickson, "Cholesterol testing on a smartphone," *Lab. Chip*, vol. 14, no. 4, pp. 759-763, Jan. 2014.

J.-H. Park, G.-T. Park, I. H. Cho, S.-M. Sim, J.-M. Yang, and D.-Y. Lee, "An antimicrobial protein, lactoferrin exists in the sweat: proteomic analysis of sweat," *Exp. Dermatol.*, vol. 20, no. 4, pp. 369-371, 2011.

J. Punter-Villagrasa, B. del Moral-Zamora, J. Colomer-Farrarons, P. Miribel-Catala, J. Cid, I. Rodriguez-Villarreal, and B. Prieto-Simon, "A portable point-of-use EIS device for in-vivo biom #x00E9; dical applications," in *2014 Conference on Design of Circuits and Integrated Circuits (DCIS)*, 2014, pp. 1-6.

I. Ramfos, N. Vassiliadis, S. Blionas, K. Efstathiou, A. Fragoso, C. K. O'Sullivan, and A. Birbas, "A compact hybrid-multiplexed potentiostat for real-time electrochemical biosensing applications," *Biosens. Bioelectron.*, vol. 47, pp. 482-489, September 2013.

A. A. Rowe, A. J. Bonham, R. J. White, M. P. Zimmer, R. J. Yadgar, T. M. Hobza, J. W. Honea, I. Ben-Yaacov, and K. W. Plaxco, "CheapStat: An Open-Source, 'Do-It-Yourself' Potentiostat for Analytical and Educational Applications," *PLoS ONE*, vol. 6, no. 9, p. e23783, September 2011.

M. Stanacevic, K. Murari, A. Rege, G. Cauwenberghs, and N. V. Thakor, "VLSI Potentiostat Array With Oversampling Gain Modulation for Wide-Range Neurotransmitter Sensing," *IEEE Trans. Biomed. Circuits Syst.*, vol. 1, no. 1, pp. 63-72, March 2007.

M. D. Steinberg, P. Kassal, I. Kereković, and I. M. Steinberg, "A wireless potentiostat for mobile chemical sensing and biosensing," *Talanta*, vol. 143, pp. 178-183, October 2015.

K. Su, Q. Zou, J. Zhou, L. Zou, H. Li, T. Wang, N. Hu, and P. Wang, "High-sensitive and high-efficient biochemical analysis method using a bionic electronic eye in combination with a smartphone-based colorimetric reader system," *Sens. Actuators B Chem.*, vol. 216, pp. 134-140, September 2015.

A. Sun, T. Wambach, A. G. Venkatesh, and D. A. Hall, "A low-cost smartphone-based electrochemical biosensor for point-of-care diagnostics," in *2014 IEEE Biomedical Circuits and Systems Conference (BioCAS)*, 2014, pp. 312-315.

A. Sun, T. Wambach, A. G. Venkatesh, and D. A. Hall, "A multitechnique reconfigurable electrochemical biosensor for integration into mobile technologies," in *2015 IEEE Biomedical Circuits and Systems Conference (BioCAS)*, 2015, pp. 1-4.

A. Sun, T. Wambach, A. G. Venkatesh, and D. A. Hall, "A multi-technique reconfigurable electrochemical biosensor: Enabling personal health monitoring in mobile devices," *IEEE Transactions on Biomedical Circuits and Systems*, manuscript submitted Feb. 7, 2016, pp. 1-11.

M. Vergani, M. Carminati, G. Ferrari, E. Landini, C. Caviglia, A. Heiskanen, C. Comminges, K. Zor, D. Sabourin, M. Dufva, M. Dimaki, R. Raiteri, U. Wollenberger, J. Emneus, and M. Sampietro, "Multichannel Bipotentiostat Integrated With a Microfluidic Platform for Electrochemical Real-Time Monitoring of Cell Cultures," *IEEE Trans. Biomed. Circuits Syst.*, vol. 6, no. 5, pp. 498-507, October 2012.

X. Wang, M. R. Gartia, J. Jiang, T.-W. Chang, J. Qian, Y. Liu, X. Liu, and G. L. Liu, "Audio jack based miniaturized mobile phone electrochemical sensing platform," *Sens. Actuators B Chem.*, vol. 209, pp. 677-685, March 2015.

B. W. Ward, J. S. Schiller, and R. A. Goodman, "Multiple Chronic Conditions Among US Adults: A 2012 Update," *Prev. Chronic. Dis.*, vol. 11, April 2014.

M. Xu, X. Luo, and J. J. Davis, "The label free picomolar detection of insulin in blood serum," Biosens. Bioelectron., vol. 39, no. 1, pp. 21-25, Jan. 2013.

W. Xu, S. Lu, Y. Chen, T. Zhao, Y. Jiang, Y. Wang, and X. Chen, "Simultaneous color sensing of O2 and pH using a smartphone," *Sens. Actuators B Chem.*, vol. 220, pp. 326-330, December 2015.

M. Zangheri, L. Cevenini, L. Anfossi, C. Baggiani, P. Simoni, F. Di Nardo, and A. Roda, "A simple and compact smartphone accessory for quantitative chemiluminescence-based lateral flow immunoassay for salivary cortisol detection," *Biosens. Bioelectron.*, vol. 64, pp. 63-68, February 2015.

D. Zhang, Y. Lu, Q. Zhang, L. Liu, S. Li, Y. Yao, J. Jiang, G. L. Liu, and Q. Liu, "Protein detecting with smartphone-controlled electrochemical impedance spectroscopy for point-of-care applications," *Sens. Actuators B Chem.*, vol. 222, pp. 994-1002, Jan. 2016.

What is claimed is:

1. A reconfigurable electrochemical biosensor for performing a plurality of measurement techniques, comprising:
   a power source;
   a single potentiostat circuit operable to perform a plurality of electrochemical detection techniques using one of at least three modes implementable by the single potentiostat circuit, comprising (i) an amperometric mode to perform an amperometric measurement, (ii) a potentiometric mode to perform a potentiometric measurement, and (iii) electrochemical impedance spectroscopy (EIS) mode, wherein the single potentiostat circuit comprises:
      two working electrodes (WE), with each WE addressable on a separate channel,
      two resistive feedback transimpedance amplifiers (RFTIA), each RFTIA connected to a respective WE, wherein each RFTIA has an independently adjustable gain and bandwidth, and wherein at least one of the two RFTIA is deactivatable based on a selected mode of the at least three modes of the implementable by the single potentiostat circuit,
      a reference electrode (RE), with the RE addressable on a separate channel,
      a counter electrode (CE), with the CE addressable on a separate channel, and
      a plurality of amplifier circuits connected to one or more of the RE or outputs, wherein the plurality of amplifier circuits are deactivatable based on a selected mode of the at least three modes implementable by the single potentiostat circuit;
   a microcontroller in communication with the single potentiostat circuit, wherein the microcontroller is configured to regulate power to control switching of the at least three modes implementable by the single potentiostat circuit;
   a digital to analog converter (DAC) in communication with the single potentiostat circuit and the microcontroller;
   an analog to digital converter (ADC) in communication with the single potentiostat circuit and the microcontroller; and
   a testing port adapted to interface with a plurality of external test strips or external electrodes.

2. The reconfigurable electrochemical biosensor of claim 1, wherein said plurality of measurement techniques are implementable without redundancy of circuit components for the plurality of measurement techniques.

3. The reconfigurable electrochemical biosensor of claim 1, wherein said plurality of measurement techniques comprise amperometric measurements, potentiometric measurements, and impedance spectroscopy.

4. The reconfigurable electrochemical biosensor of claim 1, wherein said smartphone comprises a Google's Project Ara™ smartphone.

5. The reconfigurable electrochemical biosensor of claim 1, further comprising a connection port adapted for high-speed communication with said smartphone or wearable device.

6. The reconfigurable electrochemical biosensor of claim 1, wherein said plurality of measurement techniques is selected from the group consisting of cyclic voltammetry, chronoampermetry, square wave voltammetry and differential pulse voltammetry.

7. The reconfigurable electrochemical biosensor of claim 1, wherein said reconfigurable electrochemical biosensor is implementable to perform an analysis selected from the group consisting of glucose testing, measuring pH, health and wellness monitoring, monitoring chronic illnesses, monitoring Cystic Fibrosis, monitoring inflammation, assessing food or water safety, detection of heavy metal or *salmonella* in the environment or produce, daily health tracking, measuring cholesterol or hydration levels, detecting an infectious or pathogenic agent, detecting malaria, detecting human immunodeficiency virus (HIV), detecting hepatitis C virus (HCV), and detecting tuberculosis (TB).

8. A system for performing electrochemical sensing tests, comprising:
   a portable electronic platform; and
   a reconfigurable electrochemical biosensing circuit configured to perform a plurality of measurement techniques in a plurality of modes comprising (i) an amperometric mode to perform an amperometric measurement, (ii) a potentiometric mode to perform a potentiometric measurement, and (iii) electrochemical impedance spectroscopy (EIS) mode to perform an EIS measurement, the reconfigurable electrochemical biosensing circuit comprising:
      a single potentiostat circuit, comprising (i) two working electrodes (WE), with each WE addressable on a separate channel, (ii) two resistive feedback transimpedance amplifiers (RFTIA), each RFTIA connected to a respective WE, wherein each RFTIA has an independently adjustable gain and bandwidth, and wherein at least one of the two RFTIA is deactivatable based on a selected mode of the at least three modes of the implementable by the reconfigurable electrochemical biosensing circuit, (iii) a reference electrode (RE), with the RE addressable on a separate channel, (iv) a counter electrode (CE), with the CE addressable on a separate channel, and (v) a plurality of amplifier circuits connected to one or more of the RE or outputs, wherein the plurality of amplifier circuits are deactivatable based on a selected mode of the at least three modes of the implementable by the single potentiostat circuit, a microcontroller in communication with the single potentiostat circuit, the microcontroller configured to regulate power to control switching of the at least three modes implementable by the single potentiostat circuit, a digital to analog converter (DAC) in communication with the single potentiostat circuit and the microcontroller, an analog to digital converter (ADC) in communication with the single potentiostat circuit and the microcontroller, and a testing port adapted to interface with a plurality of external test strips or external electrodes.

9. The system of claim 8, further comprising a disposable test strip configured to connect to the reconfigurable electrochemical biosensing circuit at the testing port.

10. The system of claim 8, wherein the two working electrodes are configured to be run simultaneously.

11. The system of claim 8, wherein the reference electrode and the counter electrode are configured to set a potential for the reconfigurable electrochemical biosensing circuit.

12. The system of claim 8, wherein the reconfigurable electrochemical biosensing circuit further comprises an input buffer connected to the reference electrode in the amperometric mode, and wherein the input buffer is configured as a high impedance input for an op-amp in the potentiometric mode.

13. The system of claim 8, wherein the reference electrode is configured to be floating in the EIS mode.

14. The system of claim 8, wherein a first two-electrode sensor is attached between the counter electrode and a first one of the working electrodes.

15. The system of claim 8, wherein a second two-electrode sensor is attached between the counter electrode and a second one of the working electrodes.

16. The system of claim 8, wherein the portable electronic platform comprises smartphone, smartwatch, personal digital assistant (PDA), tablet computer, textile including electronic components or any wearable technology, home appliance, vehicle or autonomous vehicle.

17. The system of claim 16, further comprising:

a connection port adapted for high-speed communication that interfaces the reconfigurable electrochemical biosensing circuit with the portable electronic platform.

* * * * *